United States Patent
Prutchi

(10) Patent No.: US 10,695,125 B2
(45) Date of Patent: Jun. 30, 2020

(54) UNIPOLAR AND/OR BIPOLAR ABLATION CATHETER

(71) Applicant: Renal Dynamics Ltd., Road Town (VG)

(72) Inventor: David Prutchi, Voorhees, NJ (US)

(73) Assignee: Renal Dynamics Ltd., Road Town (VG)

( * ) Notice: Subject to any disclaimer, the term of this patent is extended or adjusted under 35 U.S.C. 154(b) by 838 days.

(21) Appl. No.: 14/764,679

(22) PCT Filed: Jan. 30, 2014

(86) PCT No.: PCT/IB2014/058679
§ 371 (c)(1),
(2) Date: Jul. 30, 2015

(87) PCT Pub. No.: WO2014/118734
PCT Pub. Date: Aug. 7, 2014

(65) Prior Publication Data
US 2015/0351836 A1   Dec. 10, 2015

Related U.S. Application Data

(60) Provisional application No. 61/759,066, filed on Jan. 31, 2013.

(51) Int. Cl.
*A61B 18/14* (2006.01)
*A61B 5/0215* (2006.01)
(Continued)

(52) U.S. Cl.
CPC ........ *A61B 18/1492* (2013.01); *A61B 5/0215* (2013.01); *A61B 5/02416* (2013.01);
(Continued)

(58) Field of Classification Search
CPC ...... A61B 18/1492; A61B 2018/00011; A61B 2018/00214; A61B 2018/00577;
(Continued)

(56) References Cited

U.S. PATENT DOCUMENTS 5,683,366 A * 11/1997 Eggers ................... A61B 18/12
604/114
2004/0087939 A1   5/2004 Eggers et al.
(Continued)

FOREIGN PATENT DOCUMENTS

| CN | 202497235 | 10/2012 |
|----|-----------|---------|
| CN | 102781357 | 11/2012 |

(Continued)

OTHER PUBLICATIONS

Communication Relating to the Results of the Partial International Search dated May 23, 2014 From the International Searching Authority Re. Application No. PCT/IB2014/058677.
(Continued)

*Primary Examiner* — Daniel W Fowler
*Assistant Examiner* — Tigist S Demie

(57) ABSTRACT

An ablation device and/or method of ablation may include placing one or more ablation electrodes in contact with a target tissue in a lumen. An electrical insulator may be positioned between the electrode and a lumen fluid and an electrical signal (for example a radio frequency signal) may be conveyed between the electrodes to heat and/or ablate the target tissue. Ablation may be bipolar and/or an in lumen dispersive electrode may be supplied for unipolar ablation. Ablation progress may be sensed and ablation may be adjusted to produce a desired level and/or geometry and/or distribution of ablation.

17 Claims, 23 Drawing Sheets

(51) Int. Cl.
*A61B 5/024* (2006.01)
*A61B 18/00* (2006.01)
*A61B 18/12* (2006.01)
*A61B 18/16* (2006.01)
*A61B 90/00* (2016.01)

(52) U.S. Cl.
CPC .............. *A61B 2018/00011* (2013.01); *A61B 2018/00083* (2013.01); *A61B 2018/00101* (2013.01); *A61B 2018/00214* (2013.01); *A61B 2018/00267* (2013.01); *A61B 2018/00285* (2013.01); *A61B 2018/00404* (2013.01); *A61B 2018/00434* (2013.01); *A61B 2018/00511* (2013.01); *A61B 2018/00577* (2013.01); *A61B 2018/00654* (2013.01); *A61B 2018/00702* (2013.01); *A61B 2018/00821* (2013.01); *A61B 2018/00827* (2013.01); *A61B 2018/00839* (2013.01); *A61B 2018/00875* (2013.01); *A61B 2018/124* (2013.01); *A61B 2018/126* (2013.01); *A61B 2018/1253* (2013.01); *A61B 2018/162* (2013.01); *A61B 2090/065* (2016.02)

(58) Field of Classification Search
CPC ........... A61B 2018/00654; A61B 2018/00821; A61B 2018/00875; A61B 2018/124; A61B 2018/1253; A61B 2018/126; A61B 2018/162; A61B 2090/065
See application file for complete search history.

(56) References Cited

U.S. PATENT DOCUMENTS

| | | |
|---|---|---|
| 2004/0162554 A1 | 8/2004 | Lee et al. |
| 2004/0162556 A1* | 8/2004 | Swanson ............ A61B 18/1482 606/49 |
| 2008/0281322 A1 | 11/2008 | Sherman et al. |
| 2010/0018569 A1 | 1/2010 | Mitchell et al. |
| 2010/0168559 A1 | 7/2010 | Tegg et al. |
| 2010/0274238 A1 | 10/2010 | Klimovitch |
| 2011/0306851 A1 | 12/2011 | Wang |
| 2012/0029512 A1 | 2/2012 | Willard et al. |
| 2012/0101413 A1 | 4/2012 | Beetel et al. |
| 2012/0157987 A1 | 6/2012 | Steinke et al. |
| 2012/0172859 A1* | 7/2012 | Condie ............ A61B 18/1492 606/33 |
| 2012/0265066 A1 | 10/2012 | Crow et al. |
| 2012/0296232 A1 | 11/2012 | Ng |
| 2013/0096919 A1 | 4/2013 | Klassen et al. |
| 2013/0165916 A1 | 6/2013 | Mathur et al. |
| 2013/0165917 A1 | 6/2013 | Mathur et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0231658 A1 | 9/2013 | Wang et al. |
| 2013/0274658 A1 | 10/2013 | Steinke et al. |
| 2016/0008059 A1 | 1/2016 | Prutchi |

FOREIGN PATENT DOCUMENTS

| | | |
|---|---|---|
| WO | WO 2007/008954 | 1/2007 |
| WO | WO 2012/068471 | 5/2012 |
| WO | WO 2012/158864 | 11/2012 |
| WO | WO 2013/096913 | 6/2013 |
| WO | WO 2013/096916 | 6/2013 |
| WO | WO 2013/096920 | 6/2013 |
| WO | WO 2013/096922 | 6/2013 |
| WO | WO 2014/118733 | 8/2014 |
| WO | WO 2014/118785 | 8/2014 |

OTHER PUBLICATIONS

Communication Relating to the Results of the Partial International Search dated May 23, 2014 From the International Searching Authority Re. Application No. PCT/IB2014/058679.
International Preliminary Report on Patentability dated Aug. 13, 2015 From the International Bureau of WIPO Re. Application No. PCT/IB2014/058677.
International Preliminary Report on Patentability dated Aug. 13, 2015 From the International Bureau of WIPO Re. Application No. PCT/IB2014/058679.
International Search Report and the Written Opinion dated Sep. 15, 2014 From the International Searching Authority Re. Application No. PCT/IB2014/058677.
International Search Report and the Written Opinion dated Sep. 15, 2014 From the International Searching Authority Re. Application No. PCT/IB2014/058679.
Dorwarth et al. "Radiofrequency Catheter Ablation: Different Cooled and Noncooled Electrode Systems Induce Specific Lesion Geometries and Adverse Effect Profiles", PACE, 26(Pt.I): 1438-1445, Jul. 2003.
Rocha-Singh "Renal Artery Denervation: A Brave New Frontier. Emerging Therapies for Treating Patients With Severe, Treatment-Resistant Hypertension", Endovascular Today, 11: 45-52, Feb. 2012.
Restriction Official Action dated Nov. 29, 2017 From the US Patent and Trademark Office Re. U.S. Appl. No. 14/764,190. (10 Pages).
Official Action dated Nov. 4, 2019 From the US Patent and Trademark Office Re. U.S. Appl. No. 14/764,190. (12 pages).
Notification of Office Action and Search Report dated Jan. 24, 2017 From the State Intellectual Property Office of the People's Republic of China Re. Application No. 201480002839.7. (6 Pages).
Official Action dated Mar. 13, 2019 From the US Patent and Trademark Office Re. U.S. Appl. No. 14/764,190. (9 pages).

* cited by examiner

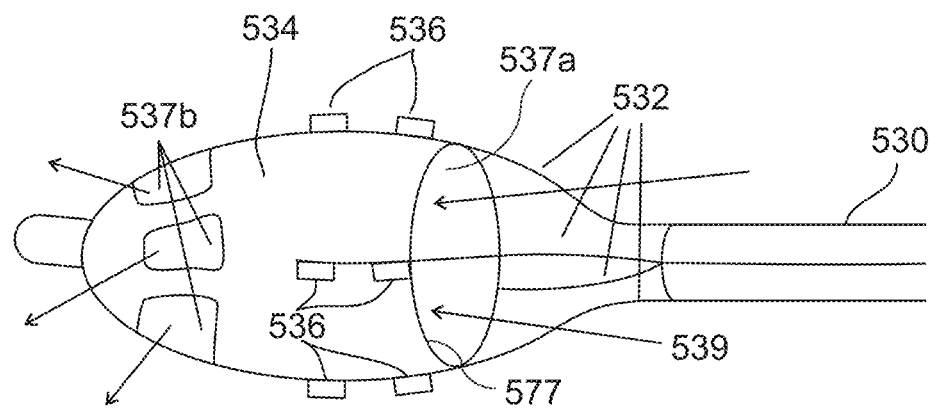
FIG. 5
FIG. 6A
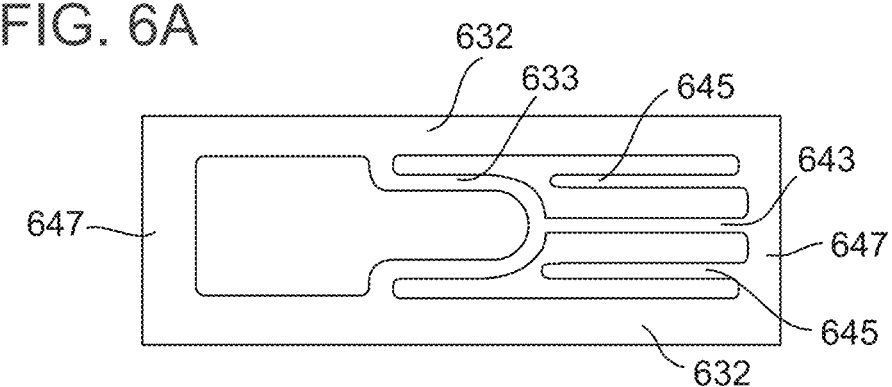
FIG. 6B
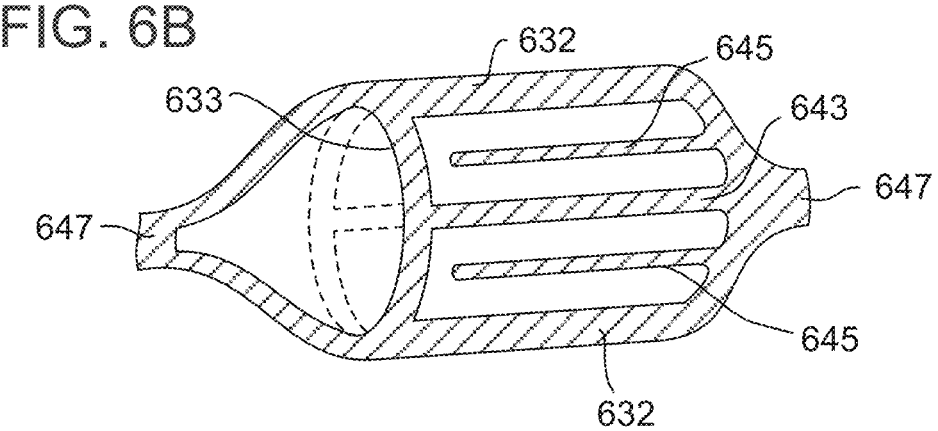

(++)

UNIPOLAR AND/OR BIPOLAR ABLATION CATHETER

RELATED APPLICATIONS

This application is a National Phase of PCT Patent Application No. PCT/IB2014/058679 having International filing date of Jan. 30, 2014, which claims the benefit of priority under 35 USC § 119(e) of U.S. Provisional Patent Application No. 61/759,066 filed on Jan. 31, 2013. The contents of the above applications are all incorporated by reference as if fully set forth herein in their entirety.

FIELD AND BACKGROUND OF THE INVENTION

The present invention, in some embodiments thereof, relates to an ablation catheter and, more particularly, but not exclusively, to a radio frequency ablation catheter that may optionally be suited for renal artery denervation.

SUMMARY OF THE INVENTION

According to an aspect of some embodiments of the present invention there is provided an ablation catheter comprising: a plurality of ablation electrodes; a dispersive electrode; one or more sensors detecting an indicator of ablation progress; and a controller programmed to: receive from the one or more sensors an indicator of progress of a bipolar ablation process between a pair of the plurality of ablation electrodes, identify a zone for further ablation from the received indicator and instruct to ablate the zone with a unipolar signal between the dispersive electrode and at least one of the plurality of ablation electrodes.

According to some embodiments of the invention, the unipolar signal is between the dispersive electrode at least one electrode from the pair of ablation electrodes.

According to some embodiments of the invention, the controller is further programmed to analyze a level of ablation from the received indicator and wherein the zone is a zone wherein the analyzed level of ablation is below a target level According to some embodiments of the invention, the controller is further programmed to instruct the bipolar ablation process.

According to some embodiments of the invention, the controller is further programmed to instruct stopping the bipolar ablation process based on the received indicator.

According to some embodiments of the invention, the controller is further programmed to select based on the output of the one or more sensors one electrode from the pair of ablation electrodes, and instruct conveying of a unipolar ablation signal between the one electrode and the dispersive electrode.

According to some embodiments of the invention, the output of the one or more sensors indicates a preliminary distribution of lesion formation in a target tissue and wherein the processor is programmed to instruct the unipolar ablation signal to achieve a predetermined distribution of lesion formation in the target tissue.

According to some embodiments of the invention, the one or more sensors detect an impedance between two electrodes selected from the plurality of ablation electrodes and the dispersive electrodes.

According to some embodiments of the invention, the controller is further programmed to: instruct conveying of an auxiliary signal between a pair of electrodes selected from the ablation electrodes and the dispersive electrode during an interruption in the bipolar ablation signal and wherein the one or more sensors are sensitive to an impedance of the auxiliary signal.

According to some embodiments of the invention, the plurality of electrodes includes at least four pairs of electrodes distributed helically along the lumen.

According to some embodiments of the invention, the controller is further programmed to evaluate a contact of an electrode with a target tissue based on an impedance of a unipolar signal between the electrode and a dispersive electrode.

According to some embodiments of the invention, the one or more sensors detect a temperature of at least one of the target tissue and at least one of the plurality of ablation electrodes.

According to some embodiments of the invention, the invention further comprises: an insulator electrically insulating at least one of the plurality of ablation electrodes from a fluid in the lumen.

According to some embodiments of the invention, the dispersive catheter is in contact with a fluid inside of the lumen.

According to some embodiments of the invention, he one or more sensors include a plurality of sensors and wherein the processor is further programmed to estimate a detected spatial distribution of a lesion in the tissue.

According to some embodiments of the invention, the processor is further programmed to instruct the ablation with a unipolar signal to modify the detected spatial distribution of lesion formation to achieve a predetermined spatial distribution of lesion formation.

According to an aspect of some embodiments of the present invention there is provided a method of ablation comprising: ablating a zone of a target tissue with a bipolar signal between two ablation electrodes; sensing an indicator of lesion formation in a subzone of the zone; and ablating the subzone with a unipolar signal between a dispersive electrode and one of the two ablation electrodes based on a result of the sensing.

According to some embodiments of the invention, the sensing includes measuring a temperature of the target tissue.

According to some embodiments of the invention, the sensing includes measuring an impedance of a signal between the one ablation electrode and the dispersive electrode.

According to some embodiments of the invention, the sensing includes measuring an impedance of a signal between the one ablation electrode and the dispersive electrode.

According to some embodiments of the invention, the signal between the one ablation electrode and the dispersive electrode is an auxiliary signal conveyed during an interruption in the ablating.

According to some embodiments of the invention, the auxiliary signal has a lower power than the bipolar signal.

According to some embodiments of the invention, the invention further comprises: estimating a level of lesion formation in the subzone and wherein the ablating is performed when the estimated level of lesion formation is less than a target level of lesion formation.

According to some embodiments of the invention, the sensing is in each of a plurality of subzones, the method further comprising: estimating a distribution of a lesion in the zone and wherein the ablating a subzone achieves a predetermined distribution of lesion in the zone.

According to some embodiments of the invention, the invention further comprises estimating, from a result of the sensing, a contact between one of the two ablation electrodes and the target tissue based on an impedance measured at the one ablation electrode.

According to some embodiments of the invention, the invention further comprising estimating an applied ablation power to the target tissue based on the estimated contact and a result of the sensing.

According to an aspect of some embodiments of the present invention there is provided an ablation catheter comprising: a plurality of ablation electrodes; and a dispersive electrode; wherein at least one of the plurality of ablation electrodes is configured to perform all of the functions of bipolar ablation and unipolar ablation and sensing an indicator of ablation progress in a single location during a single ablation session.

According to some embodiments of the invention, the at least one ablation electrode is configured to perform all of the functions of bipolar ablation and unipolar ablation and sensing an indicator of ablation progress in a single location during a single ablation session repeatedly.

According to some embodiments of the invention, the at least one ablation electrode is configured to perform all of the functions of bipolar ablation and unipolar ablation and sensing an indicator of ablation progress in a single location during a single ablation session repeatedly iteratively.

According to an aspect of some embodiments of the present invention there is provided an ablation catheter comprising: a plurality of ablation electrodes; a dispersive electrode; and a controller programmed to instruct a single ablation electrode to perform the functions of bipolar ablation and unipolar ablation and sensing an indicator of ablation progress in a single location during a single ablation session.

According to some embodiments of the invention, the controller is programmed to command the at least one ablation electrode to perform all of the functions of bipolar ablation and unipolar ablation and sensing an indicator of ablation progress in a single location during a single ablation session repeatedly.

According to some embodiments of the invention, the controller is programmed to command the at least one ablation electrode to perform all of the functions of bipolar ablation and unipolar ablation and sensing an indicator of ablation progress in a single location during a single ablation session repeatedly iteratively.

According to an aspect of some embodiments of the present invention there is provided a method of catheter ablation catheter comprising: performing bipolar ablation; performing unipolar ablation; and sensing an indicator of ablation progress in a single location during a single ablation session with using the same ablation electrode in each of the steps.

According to some embodiments of the invention, each of the steps is repeated in a single ablation session in a single location.

According to some embodiments of the invention, each of the steps is repeated iteratively in a single ablation session in a single location.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 illustrates a windsock type insulator in accordance with some embodiments of the present invention;

FIGS. 6A-B illustrate a laser-cut tube type support structure in accordance with some embodiments of the present invention;

DESCRIPTION OF SPECIFIC EMBODIMENTS OF THE INVENTION

Figure 1:
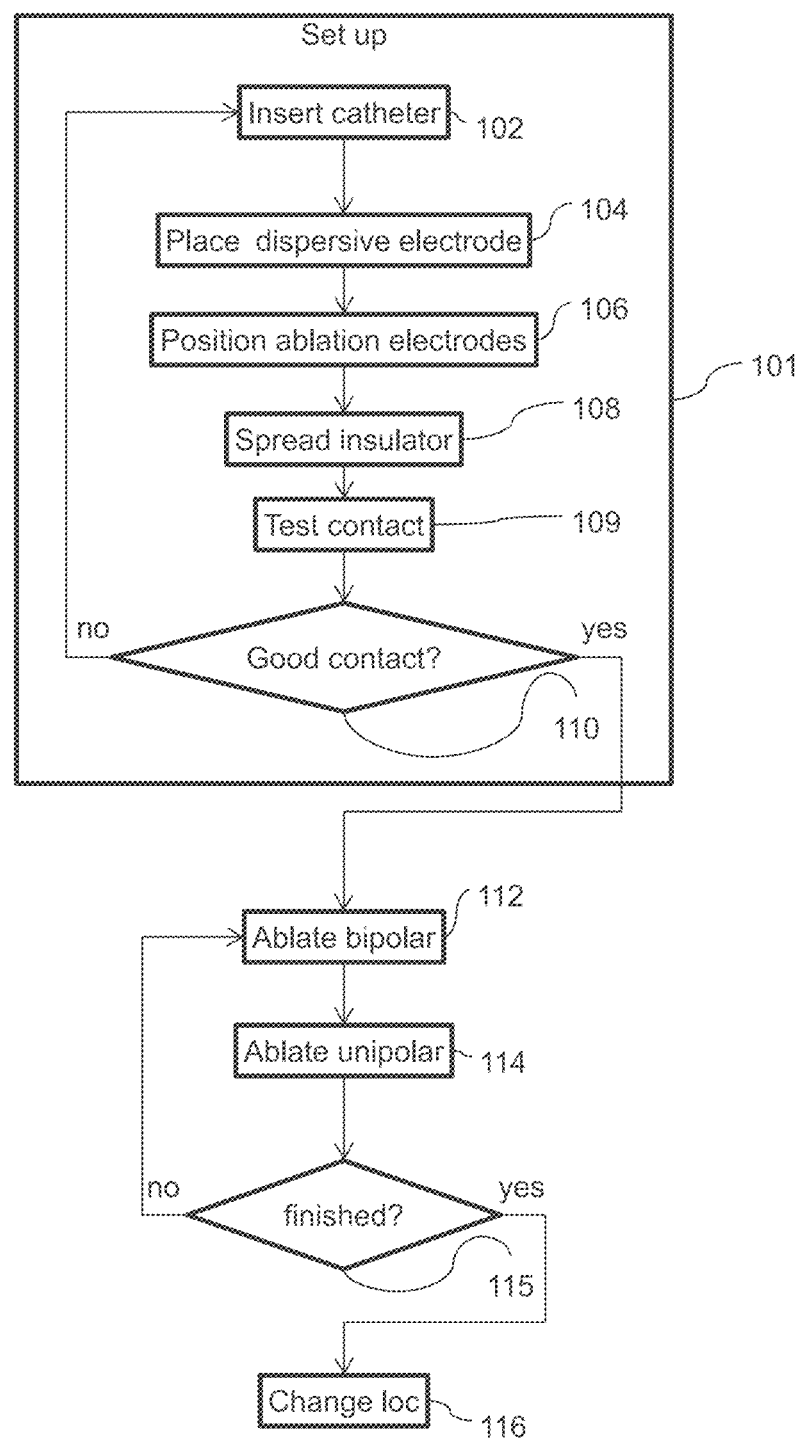
FIG. 1 is a flowchart illustrating a method of ablation in accordance with some embodiments of the present invention.

The present invention, in some embodiments thereof, relates to an ablation catheter and, more particularly, but not exclusively, to a radio frequency ('RF') ablation catheter that may optionally be used for renal artery denervation.

In some embodiments, the present invention relates to methods and/or devices (e.g., control unit) for unipolar and/or bipolar ablation using ablation catheter, e.g., RF ablation catheter.

Overview

1 Ablation Device with Electrical Insulation and Cooling

An aspect of some embodiments of the current invention relates to a method of catheter ablation wherein an ablation electrode is optionally introduced into a lumen and/or positioned in contact with a tissue to be ablated. The ablation catheter may be provided with an insulator, for example a polyurethane membrane. A first side of an insulator may be optionally held against tissue surrounding the location of the ablation electrode. The membrane may for example electrically insulate the ablation electrode and/or an ablation zone from a fluid in the lumen. The ablation zone may be heated and/or ablated by conveying an electrical signal (for example an RF signal) between the ablation electrode and a second electrode. A portion of the ablation zone may optionally be cooled. For example the insulator may transfer heat away from the electrode and/or the lesion formed by the ablation and/or the tissue in the vicinity of the electrode and/or tissue in the vicinity of the lesion. Optionally, the insulator may conduct the heat to a heat sink. For example a heat sink may include a fluid. The fluid may be located on the side of the insulator that is opposite the ablation zone. For example the heat sink may include lumen fluid (for example blood) flowing across the side of the insulator opposite the ablation zone and/or an artificial cooling fluid. The local thickness and/or heat conductivity of the insulator may optionally be adjusted to preferentially cool one portion of the ablation zone more than another portion. The insulator may optionally be held in place and/or spread out by supports to open like a tent and/or an umbrella and/or an expandable basket and/or a malecot. The support structure may optionally include for example ribs and/or stretchers like an umbrella and/or other support (e.g., brace, buttress, stanchion, cantilever, strut, frame and/or spines). The supports may include, for example, inflatable (hydraulic and/or pneumatic) supports, supports made of nitinol, a folding basket, a malecot, a stent, a folding stent, a laminated structure, a balloon and/or an expandable woven structure. The insulator may allow fluid flow through the lumen. For example, the insulator may be open at a distal end, allowing blood to continue to flow through the delivery vessel. For example, the insulator may include a passageway to allow flow past the insulator. For example the insulator may have an open ended cylindrical geometry. Fluid may optionally flow along the lumen through a passageway along the axis of the cylinder while the cylinder walls (the insulator) insulate the walls of the lumen from the fluid. Optionally, as the insulator expands, the passageway may also expand. For example the passageway may have a cross section open to flow that has an area of least 50% of the area of the cross section of the lumen that is open to flow. Alternatively or additionally the hydraulic radius of the passageway (defined for example as the four times cross sectional area divided by the wetted perimeter) by may be 70% of the hydraulic radius of the lumen. In some embodiments the cross sectional area of flow the passageway may range between 25% and 50% of the cross sectional area of flow in the lumen and/or the hydraulic radius of the pathway way may range between 50% and 70% of the hydraulic radius of the lumen.

The expanding tent, basket and/or umbrella structure may for example have a expanded width ranging for example between 4 and 8 mm and/or ranging for example between 1 and 10 mm. The length of the basket, tent and/or umbrella structure may for example range between 10 and 40 mm and/or between 20 and 30 mm.

For example, the insulator may include a membrane of thickness ranging between for example 0.1 and 0.01 mm and/or may pose impedance (against isoconductive saline solution) for example ranging between 50 to 150 k$\Omega$ at 460 kHz (e.g., 50 to 100 k$\Omega$, 100 to 150 k$\Omega$ etc.). The membrane may be made from, for example, Urethane and/or a polyurethane polymer. In some embodiments, the basket may have a diameter of less than 6 French (2 mm) when out of an intravascular delivery sheath but before expanding. In some embodiments, the basket may contract to a diameter of less than 6 French (2 mm) contracted but before being reinserted into the sheath that is commonly used to introduce a catheter to its intended delivery location within the vasculature.

2 General

Some embodiments of the current invention may include a multi-electrode ablation device. The device may be inserted into a body lumen via a catheter. At times the ablation device may be referred to as an ablation catheter or a catheter. A multi-electrode ablation catheter may be powered by a control unit. The control unit may include, for example, an RF generator. The control unit may have a number of channels that convey an electrical signal bipolarly through a target tissue between electrode pairs (for example, the ablation electrodes may be mounted on the catheter's working [distal] end), and/or unipolarly through a target tissue between an ablation electrode and a dispersive (reference) electrode (e.g., a shaft electrode in contact with lumen fluid (for example blood) and/or an external electrode). The electrodes may be activated in accordance with a switch configuration set by a multiplexer. Multiplexer RF channels may be used to transmit radio frequency (RF) ablation energy to the electrodes. The RF channels may optionally be used to transmit an auxiliary signal. For example an auxiliary signal may be used to measure impedance between pairs of electrodes. When measuring impedance a sensor may optionally include an electrode. In some embodiments a sensor for measuring impedance may include one or more of an ablation electrode and/or a dispersive electrode. For example an auxiliary signal may be similar to an ablation signal but at a lower power (optionally minimizing and/or avoiding tissue damage during measurements). The RF channels may optionally include means to measure electrode/tissue impedance. In some embodiments, measurements may be made with high accuracy and/or repeatability. The RF channels may optionally be controlled by a controller (e.g., a microcontroller and/or single-board computer). The channels may optionally be capable of generating stimulation signals to evoke a response from target tissues and/or measuring an evoked signal from the target tissue. For example, the control unit may transmit a nerve stimulating signal over an electrode (for example an electrode of the ablation catheter). For example, the control unit may evaluate an electrical signal transmitted by the target tissue and/or sensed by an electrode (for example an electrode of the ablation catheter).

Optionally a catheter according to some embodiments of the current invention may be used for renal denervation. Renal denervation, is a minimally invasive, endovascular catheter based procedure using radiofrequency ablation aimed at treating resistant hypertension. Radiofrequency pulses may be applied to the renal arteries. Ablation in some embodiments may denude nerves in the vascular wall (adventitia layer) of nerve endings. This may causes reduction of renal sympathetic afferent and efferent activity and/or blood pressure can be decreased. During the procedure, a steerable catheter with a radio frequency (RF) energy electrode tip may deliver RF energy to a renal artery via standard femoral artery access. A series of ablations may be delivered along each renal artery.

As used herein, the term "controller" may include an electric circuit that performs a logic operation on input or inputs. For example, such a controller may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations. The instructions executed by the controller may, for example, be pre-loaded into the controller or may be stored in a separate memory unit such as a RAM, a ROM, a hard disk, an optical disk, a magnetic medium, a flash memory, other permanent, fixed, or volatile memory, or any other mechanism capable of storing instructions for the controller. The controller may be customized for a particular use, or can be configured for general-purpose use and can perform different functions by executing different software.

The controller may optionally be able to calculate the temperature of some or all of the electrodes and/or near some or all of the electrodes. For example, temperature measurements may be sensed by means of the thermocouple attached to each electrode and the output of the means is forwarded to the controller for calculation. Interaction with the user (e.g., a physician performing the ablation procedure) may optionally be via a graphical user interface (GUI) presented on for example a touch screen or another display.

In some embodiments, electrode impedance measurements may be used to estimate contact (estimated contact) between electrode and tissue as surrogate for thermal contact between electrode interface and target tissue (for example a low impedance of a unipolar signal between an ablation electrode and a dispersive electrode may indicate good contact between the ablation electrode and the target tissue). In some embodiments, power being converted to heat at electrode/tissue interface may be estimated (estimated power) for example based on the estimated contact, applied power and/or electrode temperature. Together with the time of RF application to the tissue, the estimated contact and/or estimated power and/or electrode temperature may optionally be used to calculate energy transferred to target tissue and/or resulting target tissue temperature locally at individual ablation electrode locations. Optionally, the results may be reported in real-time. Optionally, based for example on the calculated cumulative energy transferred to target tissue, the duration of ablation may be controlled to achieve quality of lesion formation and/or avoid undesirable local over-ablation and/or overheating. Control algorithms may deem to have completed lesion formation successfully for example when the quality of lesion at each electrode location reaches a predetermined range.

Some embodiments of the current invention may combine a multi-electrode ablation device with blood exclusion. In some embodiments, the distance from the proximal end of the insulating basket to the distal end (toward the catheter tip) of an in-catheter dispersive electrode may range for example between 10 to 75 mm (e.g., between 10 to 15 mm, between 10 to 25 mm, between 25 to 50 mm, between 50 to 75 mm etc.). For renal artery denervation, the distance between the dispersive electrode and the proximal end of the expandable structure may range preferably between 20 to 50 mm (e.g., 20 mm, 30 mm, 40 mm, 50 mm etc.) to ensure that the dispersive electrode is within the aorta, and away from the desired ablation area within the renal artery.

Various embodiments of the current invention may be configured to fit for example in a 5 French (1.33 mm diameter) catheter with a lumen extending from the handle through the distal tip making it possible to insert it with the aid of a standard 0.014 inch (0.36 mm) guide wire. The flexibility of the assembly may optionally be compatible with applicable medical standards. A catheter (for example the various embodiments described below) may include a guidewire. For example, the guidewire may be inserted through a lumen of the catheter. Optionally, the guidewire may help position the catheter. The guidewire may optionally be able to extend past an orifice at the distal end of the catheter.

3 Bipolar and Unipolar Ablation

An aspect of some embodiments of the current invention relates to a method of catheter ablation using bipolar and/or unipolar ablation, e.g., to achieve a desired lesion geometry. For example, bipolar ablation between a first and a second ablation electrode may be used to convey an electrical signal through a target tissue to produce a lesion. Ablation may progress more quickly at the location of the first electrode than at the location of the second electrode. Bipolar ablation may optionally be paused and unipolar ablation may be initiated between the second ablation electrode and a dispersive electrode to increase progress of ablation in the vicinity of the second electrode. A balance of unipolar and/or bipolar ablation may be used to adjust a geometry of a lesion. For example, bipolar ablation may be used to achieve spreading of a lesion along a tissue surface. For example, unipolar ablation may be used to deepen a lesion.

In some cases it may be desired to ablate tissue in a given area to an effective level (for example effective ablation may occur for heating to a temperature of between 60° and 70° C. for a time between 20 and 180 sec.). Tissue and/or contact with electrodes may be heterogeneous. Tissue may heat and/or ablate unevenly. Overheating and/or over-ablating tissue may have serious consequences (for example heating to over 90° C. and/or over-ablating may cause blood coagulation and/or blood clots and/or damage to arteries and/or internal bleeding etc.). In some embodiments, the current invention may facilitate monitoring and/or control of ablation within parts of a lesion. In some embodiments, local monitoring and/or control may produce more even ablation. For example a desired level of ablation may be reached in multiple regions of a lesion without over ablating any region.

4 In-Lumen Dispersive Electrode

An aspect of some embodiments of the current invention relates to an in-lumen dispersive electrode for unipolar ablation. The dispersive electrode may be introduced into a body lumen for example by means of a catheter and/or electrical contact may be supplied by a fluid in the lumen. The dispersive electrode may optionally be inserted into the same lumen as an ablation electrode. The dispersive electrode may be part of the same catheter as an ablation electrode. Optionally, a single catheter may include a dispersive electrode and a plurality of ablation electrodes. The catheter and/or electrodes may be configured to operate in unipolar and/or bipolar modes.

In some embodiments, a control unit may supply power for ablation (for example: a radio frequency (RF) generator). For example the control unit may be a rechargeable and/or battery-powered. The ablation generator may operate for example around the 460 kHz frequency and/or ranging for example between 400 and 600 kHz or other RF frequency ranges assigned to ISM (Industrial, Scientific, and Medical) applications within the low-frequency (LF: 30 to 300 kHz), medium-frequency (300 kHz to 3 MHz), and high-frequency (HF 3 to 30 MHz) portions of the RF spectrum. The control unit may have a number of channels that allow ablation to be conducted bipolarly between electrode pairs through the target tissue. The generator may optionally be able to deliver ablation energy to be conveyed simultaneously between one, some and/or all bipolar ablation electrode pairs in the catheter. For example a catheter may include four or more bipolar ablation electrode pairs. In some embodiments, the generator may supply a maximum power of, for example, between 3-10 W per bipolar channel. The generator may optionally be able to ablate unipolarly between one, some and/or all of the contact electrodes and a dispersive electrode, e.g., catheter-borne reference in-lumen dispersive electrode. Lesion formation may for example take between 15 to 180 seconds. Each channel may have a minimum voltage compliance of 100 V. In some embodiments, the minimum voltage compliance may permit, for example, an average of between 2 and 10 W to be delivered per bipolar electrode pair presenting an impedance in the vicinity of for example 1.5 kΩ.

In some embodiments, an ablation electrode of the current invention may be made for example of between 80% and 95% Platinum and/or between 20% and 5% Iridium. The ablation electrodes may range for example between 0.5 and 4 mm long and/or have an electrically active area for example of between 0.1 and 1 mm$^2$ and/or have a diameter ranging from 0.01 to 0.05 inch (0.25 to 1.27 mm) The electrically active area of the ablation electrodes may be in contact with a target tissue. The distance between ablation electrodes may range for example between 0.5 and 3 mm or more.

In some embodiments, a dispersive electrode may for example have a length ranging for example between 4 to 20 mm and/or have a diameter ranging between 2 and 5 French (between 0.67 and 1.67 mm) The dispersive electrode may have an electrically active area ranging for example, 20 to 50 times or more than the electrically active area and/or surface of contact of the ablation electrodes. For example the electrically active area of the dispersive electrode may range between 50 to 150 mm$^2$ (e.g., between 50 to 100 mm2, between 100 to 150 mm2, between 75 to 120 mm2 etc.). Optionally the electrically active surface of the disperse electrode may be in electrical contact with a fluid in a lumen of a patient. In some embodiments, the dispersive electrode may be coated with a material such as porous titanium nitride (TiN) or iridium oxide (IrOx). The coating may increase microscopic surface area of the electrode in electrical contact with lumen fluid.

5 Local Measurement of Ablation Progress

An aspect of some embodiments of the current invention relates to a method of catheter ablation wherein ablation progress may be measured locally at the site of one, some and/or all ablation electrodes. For example, during a pause in the bipolar ablation signal, impedance may be measured locally at an ablation electrode for example by measuring impedance between the ablation electrode and a dispersive electrode.

For example, the system may measure the complex bipolar and unipolar electrode impedance at the ablation frequency. Optionally when not ablating, an auxiliary signal may include an auxiliary current not meant to cause significant physiological effect. Electrode Impedance measurements may optionally be possible within the 100Ω to 1 kΩ range within a minimum accuracy ranging for example between 2 to 10%, and within the 100Ω to 2 kΩ range with a minimum accuracy ranging for example between 5 to 20% Minimum repeatability within the 100Ω to 2 kΩ range may range for example between 2 to 10%. Ablation interruptions may range from 1 to 100 ms when measuring unipolar impedance during bipolar ablation segments Impedance measurements may be taken at a minimum rate ranging for example between 50 to 200 samples for use by the control algorithm.

In some embodiments, temperature may be measured individually at one, some and/or all of the contact electrodes. Temperature measurements may use, for example, a thermocouple. The thermocouple may optionally be formed between the main electrode's wire and an auxiliary thermocouple wire. Temperature measurement range may be for example between 30° C. to 100° C. or more. Temperature measurement accuracy range between ±0.2 to ±1° C. or may be more accurate. Temperature measurement repeatability may range for example between 0.1 to 0.5° C. or less. Target temperatures may range for example between 60 to 80° C.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Embodiments

1 Outline of Method of Ablation

Referring now to the drawings, FIG. 1 is a flow chart illustration of an exemplary embodiment of a method of therapy using unipolar and/or bipolar ablation, in accordance with some embodiments of the invention. The exemplary method, illustrated for example in FIG. 1, of unipolar and bipolar ablation may be used to achieve a desired lesion geometry, to measure the progress of ablation locally near electrodes and/or in an area between electrodes and/or to adjust a geometry of a lesion. The method may be used to control power and duration of ablation at one or more electrodes, e.g., to ensure quality of lesion formation.

In some embodiments, an ablation device may be set up 101. In some embodiments, a catheter with the ablation device may be inserted 102 into a patient. A dispersive electrode may be optionally placed 104 in contact with a large area of the patient. Optionally, the dispersive electrode may be inserted into the patient with the catheter (e.g., the dispersive electrode may be part of the catheter). Alternatively or additionally the dispersive electrode may be independent of the catheter. The large contact area, for example the contact area may range between 50 to 150 $cm^2$ or more of the dispersive electrode may reduce tissue damage and/or impedance in the vicinity of the dispersive electrode.

In some embodiments, a two or more ablation electrodes may be positioned 106 in contact with a target tissue in an area to be ablated. The ablation electrodes may have a small contact area with the target tissue. Current flowing from the ablation electrode may be concentrated in the small contact area causing local ablation. The high current flowing through a small contact area in the vicinity of the ablation electrode may produce a high electrical impedance in the vicinity of the ablation electrode. For example, most of the impedance for current between the dispersive electrode and the ablation electrode may occur in the vicinity of the ablation electrode.

The ablation device may optionally include an insulator. The insulator may optionally be spread 108 across a surface of a target tissue. Optionally, the insulator may isolate the electrode from a fluid in a lumen (for example blood in an artery). Optionally, the insulator may prevent leaking and/or or shunting of ablative energy away from a target.

In some embodiments, after positions 106 the ablation electrodes and/or spreading 108 the insulator, the contact of the ablation electrodes with the target tissue may be tested 109. For example, the impedance may be measured between the ablation electrode and the dispersive electrode and/or the temperature may be tested at the ablation electrode while applying current. If the contact is not good 110 (Step 110: no) (for example the impendence is high) then the ablation electrode may be repositioned (for example by re-inserting 102 the catheter and/or moving and/or re-positioning 106 the ablation electrodes).

In some embodiments, once the ablation electrodes are properly positioned and/or contact is good 110 (Step 110: yes), ablation may proceed. For example, bipolar ablation 112 may take place between two ablation electrodes (note as used herein bipolar ablation may also include multipolar ablation between more than two ablation electrodes). Optional details of bipolar ablation 112 are described, for example, in FIG. 2. In some embodiments, unipolar ablation 114 may take place between one or more ablation electrodes and a dispersive reference electrode. For example, if during bipolar ablation 112 it is observed that ablation is proceeding faster near one of the ablation electrodes than near the other electrode of the pair and/or that one electrode is heating up too much and/or that ablation is taking place too near the surface etc., bipolar ablation 112 may be interrupted (for example not passing current and/or passing a reduced current) and/or optionally the fast and/or overheating electrode may be allowed to rest (for example not passing current or passing a reduced current). Unipolar ablation 114 may optionally continue at all or some of the electrodes. One or more rounds of bipolar ablation 112 and/or rest and/or unipolar ablation 114 may continue (Step 115: no) until the ablation is finished (Step 115: yes). When ablation is finished at a given location, the process may be repeated at another location 116.

2 Bipolar Ablation

Figure 2:
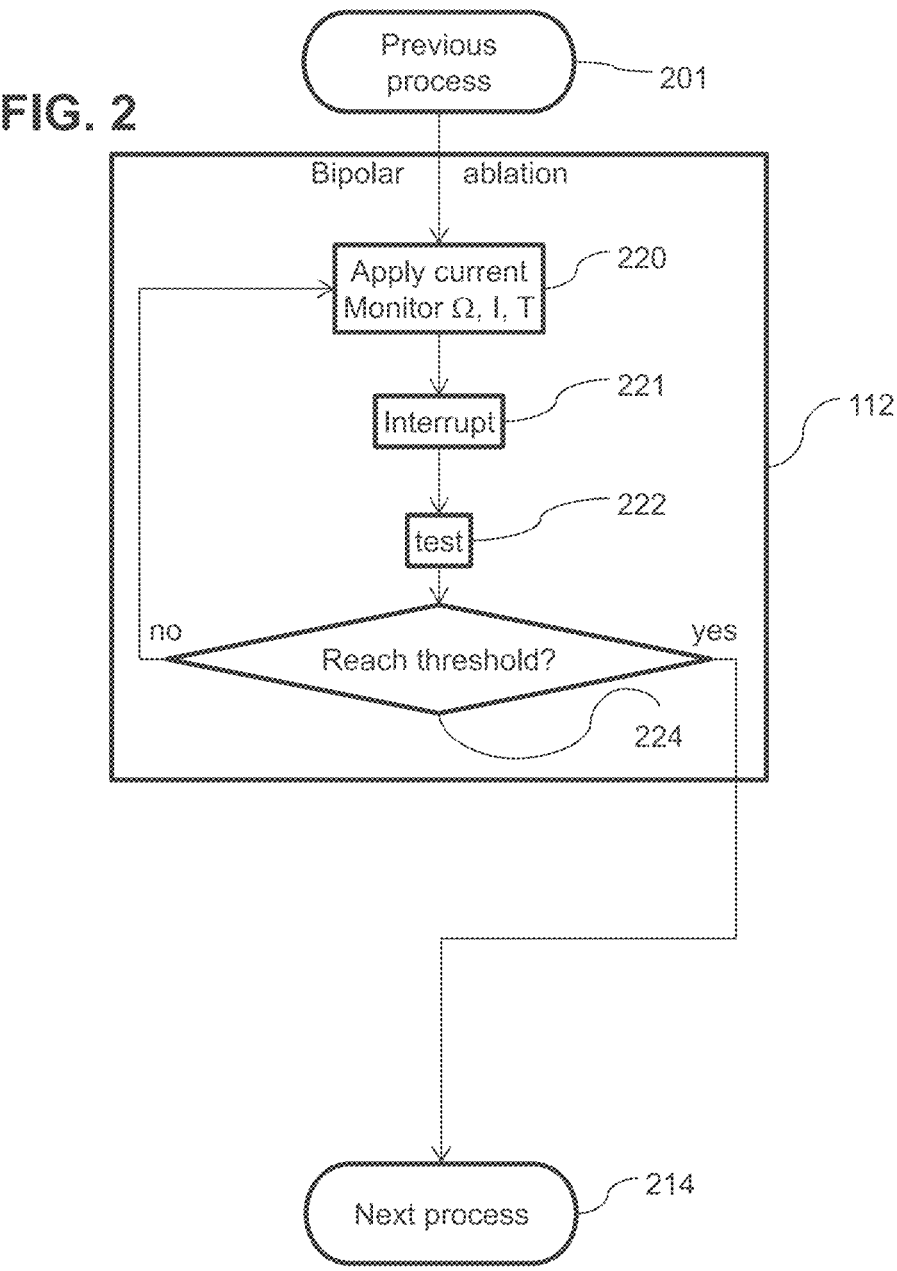
FIG. 2 is a flowchart illustrating a method of bipolar ablation in accordance with some embodiments of the present invention.

FIG. 2 is a flow chart illustration of a method of bipolar ablation in accordance with some embodiments of the current invention. Bipolar ablation 112 may optionally start after prior processes 201 as illustrated for example in FIG. 1. Bipolar (or multipolar) ablation 112 may proceed by applying a high current 220, e.g. resulting in the desired power delivered to the tissue, for example, an average of between 2 and 10 W (e.g., 2 W, 4 W, 5 W, 10 W etc.) between one or more pairs of ablation electrodes. During the application of current 220, the temperature at one, some or all of the ablation electrodes and/or the current and/or the impedance between pairs of electrodes may optionally be monitored. Application of current may continue for example between 5-200 milliseconds (e.g., 50-200 milliseconds, 100-200 milliseconds, 150-200 milliseconds etc.) at a power ranging for example between 2.0 to 10 WATT between each pair of ablation electrodes. Current application may be interrupted 221 for a short period, for example between 50-200 milliseconds at which time impedance and/or temperature may be tested 222 (e.g. measured) at the location of one or more of the ablation electrodes and/or other locations. For example, impedance may be tested 222. Optionally when testing impedance a sensor may include an electrode, for example an ablation electrode and/or a dispersive electrode. Testing 222 may optionally include measuring an impedance. For example measuring impedance may include applying a small current between the ablation electrode and a dispersive electrode. Testing 222 may include evaluating "quality of lesion" formula which may be some function of impedance, temperature, and/or energy delivered After testing 222, application 220 of current may optionally continue (for example if ablation has not been completed and/or if there are no signs of overheating and/or over-ablation) (step 224 no). The interruption of current application 220 may optionally be short enough that the target tissue does not significantly cool and/or ablation is not adversely affected. Optionally, when ablation at a particular location reaches a desired level and/or ablation and/or temperature at a location reaches a safety limit (step 224 yes), bipolar ablation 112 at that location may stop. The total length of the bipolar ablation 112 at a single location may range for example between 15-300 sec. Bipolar ablation may continue at other locations and/or a next process 214 may start.

3 Unipolar Ablation

Figure 3:
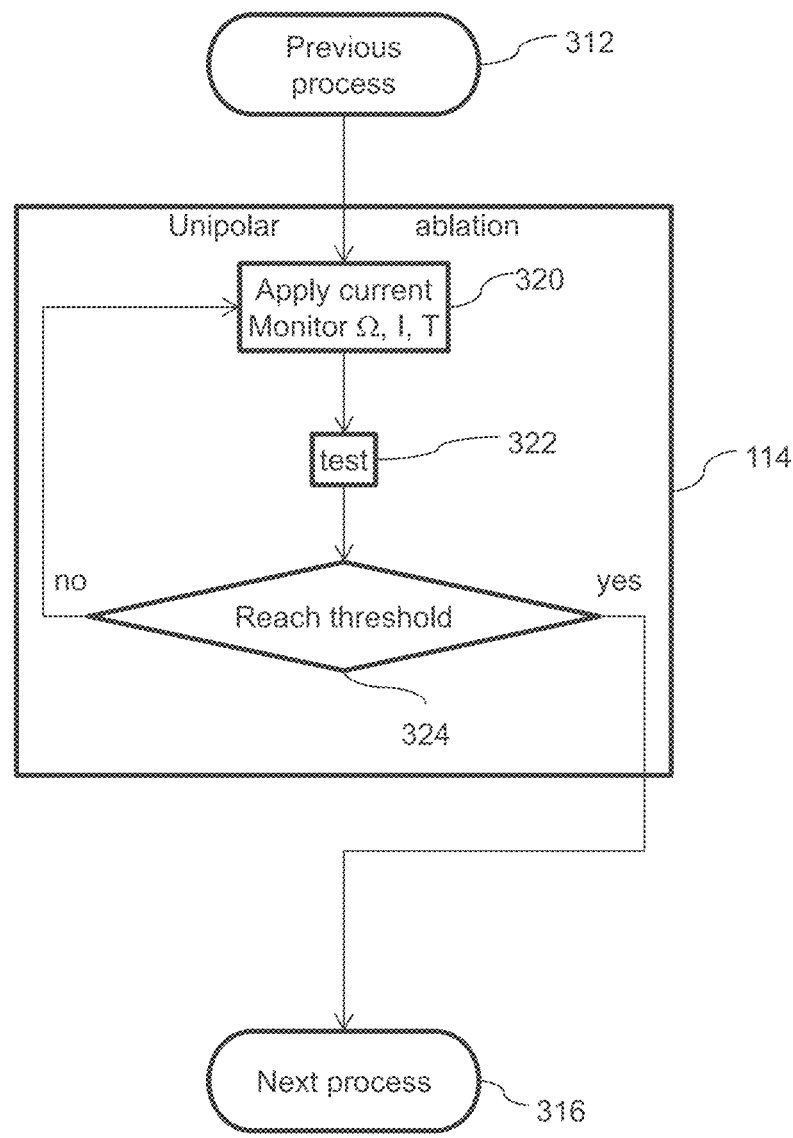
FIG. 3 is a flowchart illustrating a method of unipolar ablation in accordance with some embodiments of the present invention.

FIG. 3 is a flow chart illustration of a method of unipolar ablation in accordance with some embodiments of the current invention. Unipolar ablation may be performed by passing current between for example an ablation electrode (e.g., an ablation electrode of a pair) and a dispersive electrode. Optionally, the dispersive electrode may have a large area of contact with the patient. Typically the majority of the impedance and/or ablation occur at the location and/or near the ablation electrode. Sometimes, unipolar ablation may cause deeper lesions than bipolar ablation. In some embodiments, unipolar ablation may be used to preferentially ablate tissue at a single location and/or to achieve a preferred ablation geometry, for example to achieve a deeper lesion.

Unipolar ablation may optionally follow after a previous process 312. For example, after bipolar ablation achieves a large and/or shallow and/or heterogeneous lesion, unipolar ablation may be used to ablate a small area and/or to achieve a deeper lesion and/or even out a lesion (for example to ablate a portion of a less well done portion of a lesion).

Unipolar ablation 114 may proceed by applying a high current 320, e.g. resulting in the desired power delivered to the tissue, for example, an average of between 2 and 10 W (e.g., 2 W, 4 W, 5 W, 10 W etc.) between one or more ablation electrodes and a dispersive electrode. During the application of current 320, the temperature at one, some or all of the ablation electrodes and/or the current and/or the impedance between the electrodes (e.g., an ablation electrode and dispersive electrode) may optionally be monitored. Application of current may continue for example between 50-200 milliseconds and/or between 200 milliseconds and 20 seconds and/or between 20 seconds and 200 seconds at a power of 0.5-10 WATT between each ablation electrode and the dispersive electrode. High current application may be interrupted for a short period for example between 0.5-100 milliseconds at which time impedance and/or temperature may be tested 322 (e.g. measured) at the location of one or more of the ablation electrodes and/or other locations. Optionally when testing impedance a sensor may include an electrode, for example an ablation electrode and/or a dispersive electrode. For example, local impedance may be tested 322 by applying a small current between one of the ablation electrodes and the dispersive electrode. After testing 322, application 320 of current may optionally be resumed (step 324 no) (for example if local ablation has not been completed and/or if there are no signs of local overheating and/or over-ablation). The interruption of current application 320 may optionally be short enough that the target tissue does not significantly cool and/or ablation is not adversely affected.

In some embodiments, when ablation at a particular location reaches a desired level and/or ablation and/or temperature at a location reaches a safety limit (step 324 yes) unipolar ablation 114 at that location may be stopped. Unipolar ablation 114 may continue at other locations or other ablation electrodes and/or a next process 316 may start. For example, bipolar ablation may proceed between two electrodes until ablation reached a desired limit and/or a safety limit (step 324 yes) at some location in the zone around and/or between the two electrodes (for example ablation may reach a limit in a subzone near a first of two electrodes). Bipolar ablation may be stopped. A unipolar auxiliary signal may be conveyed from a dispersive electrode to each of the two electrodes. Based on the impedance to the auxiliary signal a subzone may be indentified for further ablation. For example a higher unipolar impedance at the first electrode than at the second electrode may indicate a lower ablation level in a subzone near the second electrode than in a subzone near the first electrode. The difference in impedance at the two electrodes may indicate an uneven distribution of ablation level and/or lesion formation in the zone. Ablation may optionally be continued at the second of the two electrodes. For example, unipolar ablation may be used in order to "touch up" the ablation in the subzone near the second electrode. For example the unipolar ablation may modify the indicated distribution to achieve a predetermined (for example even) distribution of ablation level and/or lesion formation in the zone of the two electrodes. Alternatively or additionally, bipolar ablation may continue between the second electrode and another ablation electrode.

According to some embodiments of the current invention, all and/or any portion of the steps of FIGS. 1-3 may be carried out in a single ablation session and/or while the ablation catheter and/or the electrodes remain in the same position. For example a single session may last for a time period ranging between 15 minutes to two hours (e.g. 15 minutes to 30 minutes, 30 minutes to an hour, an hour to two hours). For example a single ablative electrode may perform at a single location during a single session any, some and/or all of the functions of bipolar ablation and/or unipolar ablation and/or sensing an indicator of ablation progress and/or sensing an indicator of lesion formation. The sensing may be for example by sensing an impedance. Optionally the impedance may be to a unipolar signal and/or to a bipolar signal. The signal may include for example an ablation signal and/or an auxiliary signal. Optionally the functions may be preformed serially in any order. In some embodiments, some of the functions may be performed simultaneously.

4 Exemplary Ablation Devices

FIGS. 4A-16C illustrate various embodiments of ablation devices and/or insulators in accordance with some embodiments of the current invention. An ablation device may optionally include an insulator, for example a membrane and/or a frame. In some embodiments, the insulator may optionally be designed to press against a wall of a lumen or vessel in the vicinity of an ablation target. For example a frame may insulate from the lumen fluid an area ranging between 0.1 $mm^2$ and 40 $mm^2$ around one or more electrodes. In some embodiments, expansion of a support structure may press an insulator against an inner wall of a lumen.

Figure 4A:
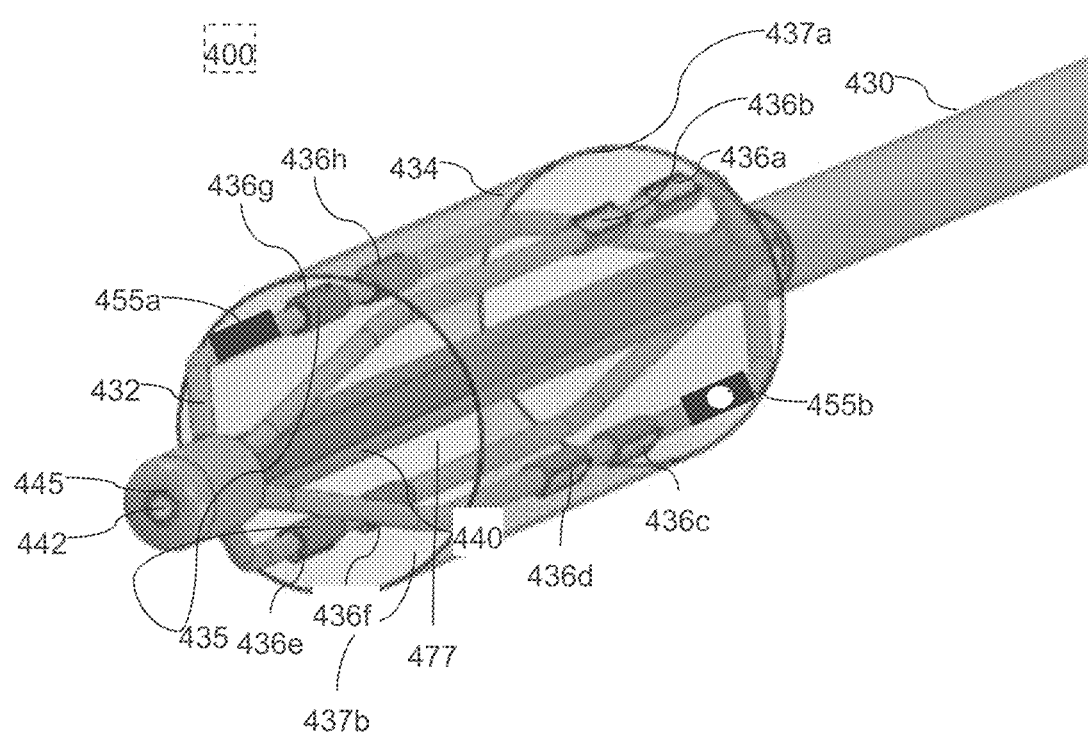
FIGS. 4A-D are illustrations of an ablation device in accordance with some embodiments of the present invention.
Figure 4B:
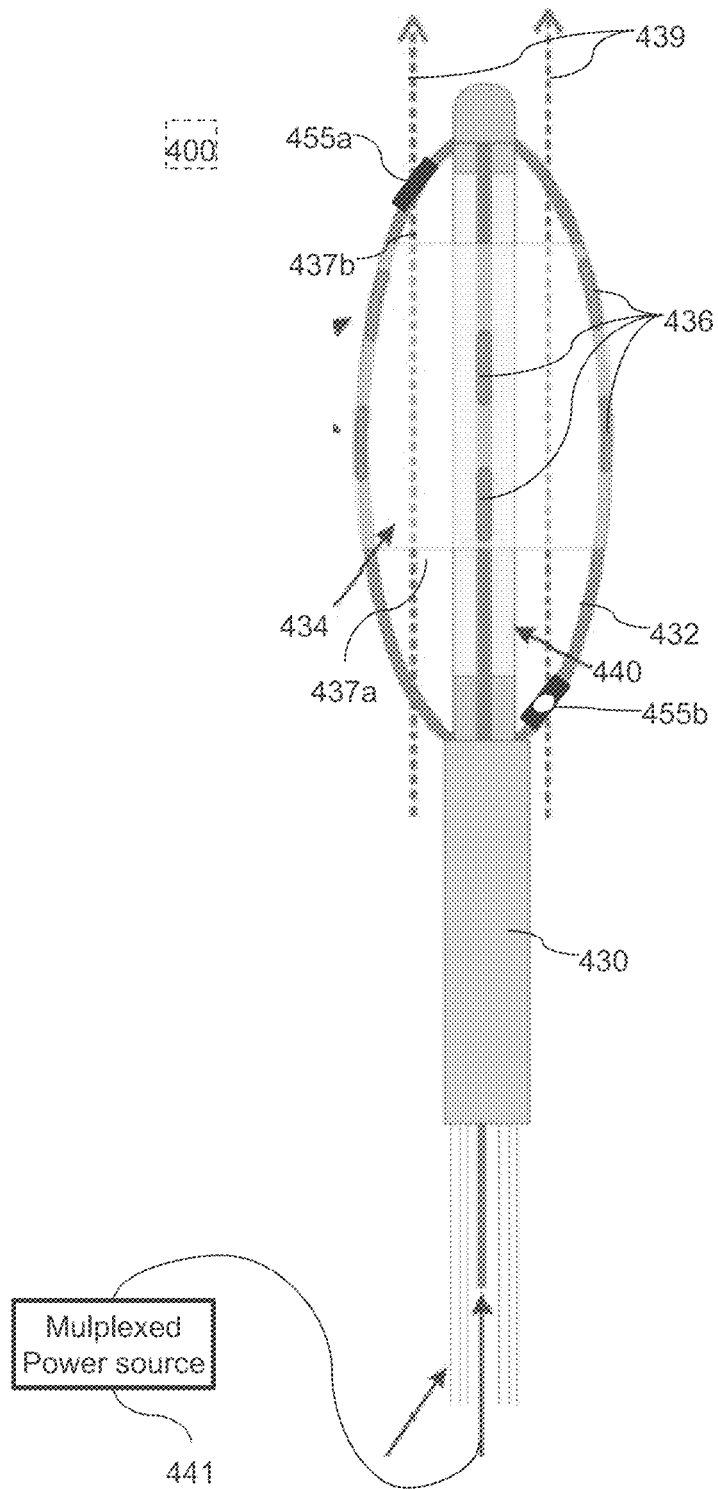
Figure 4C:
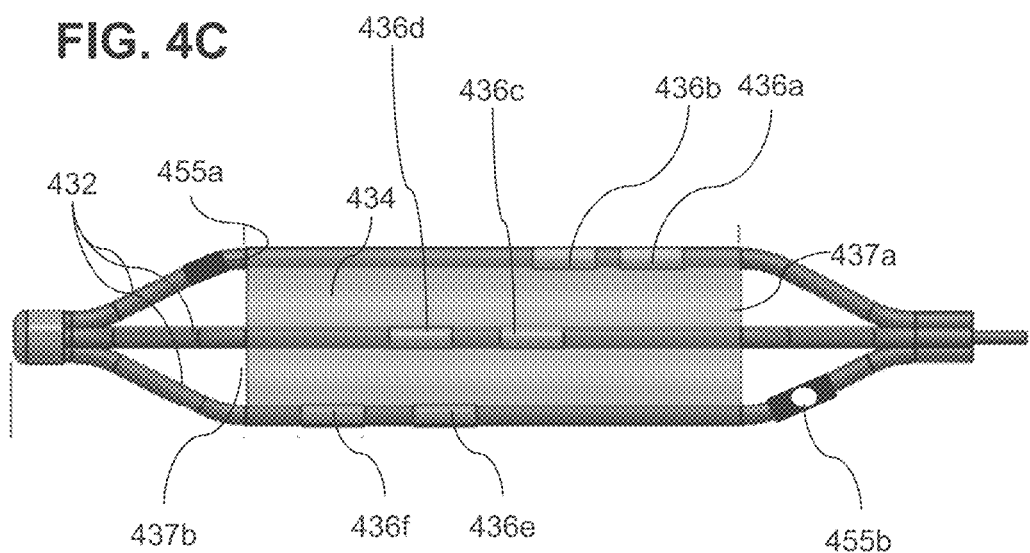
Figure 4D:
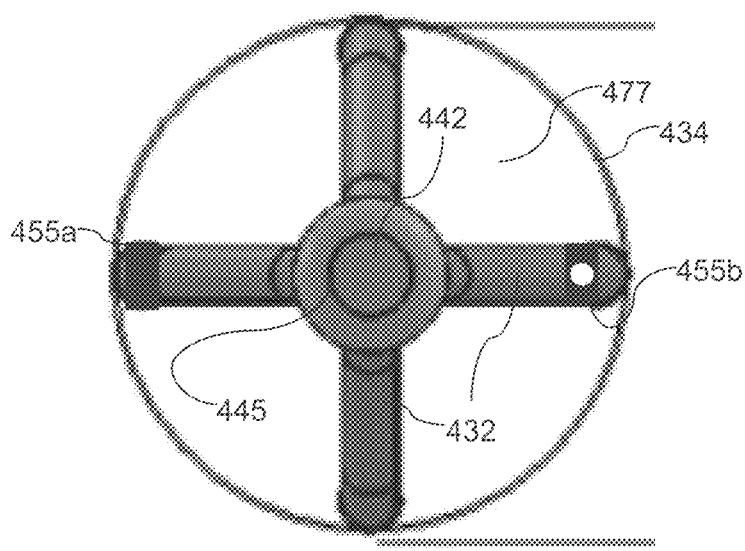
Figure 7:
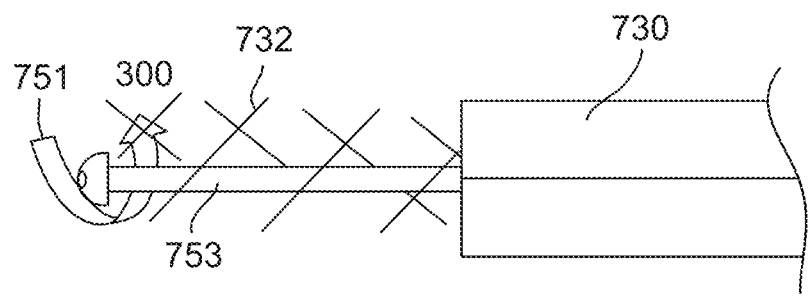
FIG. 7 is an illustration of a support structure formed of spiral wire in accordance with some embodiments of the present invention.

FIGS. 4A-C illustrates a schematic view of an exemplary ablation device 400, in accordance with some embodiments of the current invention. In some embodiments, an ablation catheter may be inserted into a lumen and/or opened to contact a target tissue. The ablation device may include an insulator that may optionally prevent shunting of ablation energy away from a target tissue and/or may cool a portion of the ablation zone. For example, the insulator may transfer heat to a heat sink. For example, heat transfer may be by conduction. For example the heat sink may include fluid flowing past the ablation zone cooling a surface of the insulator opposite the ablation zone. Optionally, a highly heat conductive material (for example metal) may be added to the insulator in a certain location to preferentially cool that location and/or the insulator may be made thinner in a particular location to allow more heat conduction away from that location. In some embodiments, the ablation catheter may include a plurality of ablation electrodes (optionally the ablation electrodes may be configured to contact a target tissue) and/or one or more dispersive electrodes (optionally a dispersive electrode may have large surface area). The dispersive electrode may provide a unipolar reference. The dispersive electrode may optionally be inserted into the lumen with the ablation electrodes. Optionally, the dispersive electrode may be in electrical contact with fluid (for example blood) within the lumen. For example, the dispersive electrode may surround the ablation catheter's shaft.

Some embodiments of an ablation device may optionally include an electrical insulator. For example, an insulator may include a membrane 434 that is spread against a target tissue. Membrane 434 may optionally prevent shunting of ablation energy away from the target tissue. For example, membrane 434 may optionally prevent shunting of ablation energy from an ablation electrode (for example one or more of electrodes 436a-h) into a fluid in vicinity of the electrode (for example, blood). In some embodiments, an ablation electrode 436a-h may optionally be coated with a non-electrically conductive material 435 except for the segment that protrudes through the blood-exclusion membrane to contact the target tissue. In some embodiments, decreasing shunting may decrease the power necessary for ablation and/or increase the control and/or precision of measurement of the power applied to the target tissue.

Membrane 434 may optionally allow fluid to flow 439 (for example see FIG. 4B) along the lumen. For example, membrane 434 may have an open cylindrical form allowing fluid flow 439 along a passageway 477 along the axis of the cylinder. Membrane 434 may optionally transfer heat away from the ablation zone. For example membrane 434 may conduct heat to fluid flowing 439 in passageway 477. For example, blood flow 439 across the inside surface of the insulator (opposite the target tissue) may cool the outside surface that is against the target tissue and/or a portion of the target tissue. By cooling the target tissue, the lesion may be made deeper and/or more even (as has been observed for example in irrigated ablation procedures). Alternatively or additionally, blood flow 439 across the inside surface of the insulator may cool some or all of electrodes 436a-h. Reducing the temperature of an electrode 436a-h may reduce the temperature in the interface between electrode 436a-h and the tissue. Reducing the temperature at the tissue electrode interface may allow more power to be delivered deeper into the tissue. Alternatively or additionally, allowing fluid flow 439 in the lumen may reduce pain and/or secondary tissue damage due to blockage of circulation during the ablation procedure.

In some embodiments, a ablation device may include one or more markers. For example, device 400 includes two individually recognizable radio opaque markers 455a,b. Markers 455a,b may optionally be easily recognized in radiographic and/or other extra body images (for example an image may be made using ultrasound and/or magnetic resonance MRI and/or x-ray and/or other imaging techniques). Distinguishing markers 455a,b may help a clinician locate and/or determine the orientation of a catheter and/or a support structure and/or each individual of electrodes 436a-h.

In some embodiments, a guidewire 442 may be inserted through a lumen of the catheter. For example, guidewire 442 may help position the catheter. Guidewire 442 may optionally be able to extend past an orifice 445 at the distal end of the catheter.

In some embodiments, a dispersive electrode 440 may be inserted into a lumen in the patient being treated. For example, in device 400, dispersive electrode 440 may be inserted into the same lumen as ablation electrodes 436a-h. Dispersive electrode 440 may optionally have a large surface of contact. For example, dispersive electrode 440 may be in contact with fluid inside the lumen. The large contact area may decrease local impedance and/or heating near dispersive electrode 440. Dispersive electrode 440 may optionally be coated with a material such as porous titanium nitride (TiN) or iridium oxide (IrOx) for example to increase its microscopic surface area in electrical contact with the fluid. Dispersive electrode 440 may optionally be a sensor for example for sensing a impedance and/or an electrode used for unipolar ablation. For example electrode 440 may be used to sense an impedance between dispersive electrode 440 and one of ablation electrodes 435a-h.

Ablation device 400 may optionally include a plurality of ablation electrodes. Ablation electrodes 436a-h may optionally be used in pairs for bipolar ablation. Alternatively or additionally, ablation electrodes 436a-h may optionally be sensors, for example to sense an impedance between a pair of ablation electrodes 436a-h. Optionally a signal may be conveyed between a pair of nearby ablation electrodes (for example between electrodes 436a and 436b and/or between electrodes 436c and 435d). Alternatively or additionally a signal may be conveyed between more distant ablation electrodes (for example between electrodes 436a and 436e and/or between electrodes 436b and 436d) Dispersive electrode 440 may be used for example to pass a high current to one, some or all of the ablation electrodes to perform unipolar ablation. Dispersive electrode 440 may optionally be used for measuring the local impedance near one or more of the ablation electrodes 436a-h. For example a small current may be passed between dispersive electrode 440 and one of the ablation electrodes 436a-h to test impedance in the local area of the ablation electrode. An optional multiplexed power source 441 (e.g. current source) (for example see FIG. 4B) may be used to supply current to a selected group of electrodes (for example including some or all of ablation electrodes 436a-h and/or dispersive electrode 440) during a time slice and/or a different group of electrodes (for example including some or all of ablation electrodes 436a-h and/or dispersive electrode 440) during a different time slice.

For example, ablation device 400 may optionally include a "basket" made out of nitinol wire spines and/or supports 432. Ablation electrodes 436a-h may optionally be positioned on supports 432. For example pairs of ablation electrodes 436a,b; 436c,b; 436e,f and 436g,h may be distributed along the periphery of the basket to ablate the intrabody target tissue. Optionally, some or all of electrodes 436a-h may be fitted with a thermocouple and/or other suitable sensor.

For example, an insulator may include a polyurethane membrane 434. Membrane 434 may be is placed onto the supports 432. Upon deployment, the basket including supports 432 and/or membrane 434 may optionally open up like an umbrella. In the exemplary embodiment, ablation electrodes 436a-h may optionally be exposed to target tissue on the inner walls of the lumen into which the catheter is deployed.

The insulator may optionally include non-porous membrane 434 covering the mid-section of the expandable basket structure. The membrane may optionally separate blood from the treatment area. Membrane 434 may optionally increase the portion of electrical ablation energy delivered to the target tissue for example by reducing the shunting of the ablation energy to the blood. In contrast to some occluding means to exclude blood (for example balloons), the basket and/or membrane 434 may be open at the distal and/or proximal ends, allowing blood to continue to flow 439 through the lumen (for example the delivery vessel and/or artery). During the ablation procedure tissue and/or organs may continue to receive blood. During the ablation procedure blood passing along the inside surface of membrane 434 may cool the surface of the target tissue.

In some embodiments, an ablation catheter may include a plurality of ablation electrode pairs. For example ablation device 400 may include four pairs of ablation electrodes 436*a-h* helically distributed around an open cylindrical basket near the end of a catheter shaft 430 (as illustrated for example in FIG. 4A). During ablation, some or all of the four pairs of ablation electrodes 436*a-h* may be activated simultaneously. For example, four lesions can be made simultaneously in a helical pattern along the wall of a lumen. Additionally, ablation current may be delivered between ablation electrodes on adjacent spines, for example between electrodes 436*b* and 436*c*, between electrodes 436*d* and 436*e*, etc.

In some embodiments, flow 439 in a lumen may help hold membrane 434 in an expanded configuration. For example, as shown in FIG. 4B, the downstream (distal) opening 437*b* of membrane 434 may be narrower than the upstream (proximal) opening 437*a*. When placed inside an artery, downstream opening 437*b* may present resistance against blood flow 439. Resistance to flow 439 exiting membrane 434 may cause pressure within membrane 434 to increase. Increased internal pressure may make membrane 434 expand against an artery wall and/or spread out, for example like a parachute and/or a windsock.

FIG. 5 illustrates an insulator 534 in the form of a windsock and/or a parachute deployed from a catheter 530 in accordance with some embodiments of the current invention. Optionally fluid may flow 539 through a passageway 577 through insulator 534. For example fluid may enter a large opening 537*a* (illustrated for example at the proximal end of insulator 534). Optionally the fluid may exit a smaller opening 537*b* (for example windows at the distal end of insulator 534). The dynamic pressure of the fluid flow 539 (for example blood flow in an artery) may help keep the insulator 534 inflated. For example, fluid pressure may press insulator 534 against walls of a lumen. Optionally, insulator 534 and/or other structural members 532 may insulate electrodes 536 from lumen fluids. Internal pressure may optionally be used to cause expansion on its own or along with another mechanism. In some embodiments, pressure against an inner wall of a lumen may be augmented by structural members. Some structural members may carry an electrode. Alternatively or additionally some structural members that do not carry electrodes may be introduced for example to provide support for the insulator. For example, in the exemplary embodiment of FIGS. 6A and 6B, a basket may be formed by cutting out from a nitinol tube. The deploying of the basket may optionally include supports springing out (where the direction of expansion has been determined by heat setting the memory of the nitinol wire). FIG. 6A illustrates the basket in a collapsed configuration and FIG. 6B illustrates the basket in an expanded configuration. Production of the tube and/or the cutting may optionally be similarly to production of a stent. The basket may include various structural elements, for example struts 632, cross members 633, support members 643, end members 647 and/or cantilever members 645. Supports 643 may for example retain a preferred geometry of other structural members and/or also provide a support for the geometry of the insulator. Cantilever members may for example supply pressure on parts of the insulator.

In some embodiments, support for electrodes and/or an insulator may be supplied by a spiral wire basket. For example as shown in the exemplary embodiment of FIG. 7 a spiral element 732 may be expanded by twisting in one direction 751 and/or collapsed by twisting in the opposite direction. Optionally, an axial wire 753 may be used for twisting spiral element 732. For example, spiral element 732 may be located at the distal end of a catheter 730. Catheter 730 may include multiple spiral elements and/or other elements that may be expanded and/or collapsed to form a desired shape. The expanding elements may optionally cause an insulating membrane to take a circular cross section and/or press an insulating membrane against the walls of a lumen. The resulting shape of the expanded membrane may depend on the way in which the spiral elements of the basket deploy. In some embodiments, electrodes and/or markers and/or an insulating frame and/or an insulating membrane may be mounted and/or included on element 732.

Figure 8:
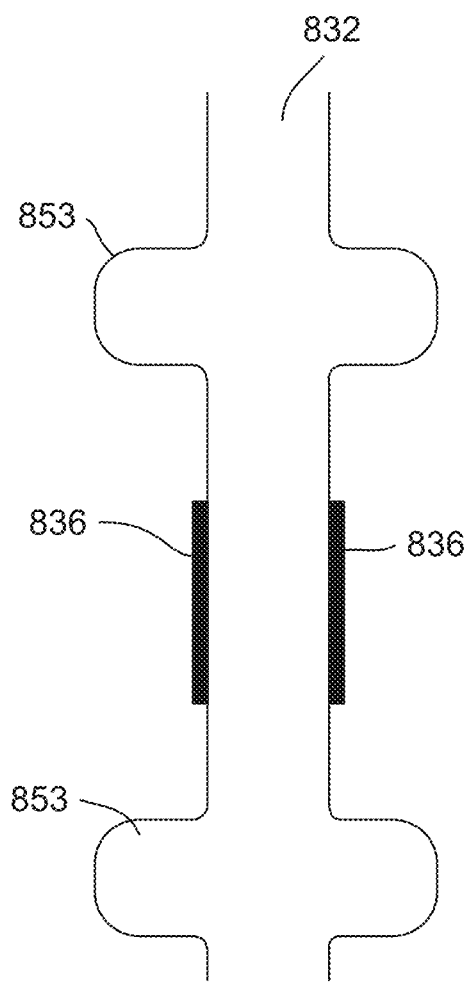
FIG. 8 is a an illustration of an insulating frame in accordance with some embodiments of the present invention.

In some embodiments, support members for an insulator may extend around an electrode, for example as illustrated in FIG. 8. Optionally, a strut 832 may hold an electrode 836 and/or a frame 853 against a tissue to be ablated. Frame 853 may optionally electrically insulate electrode 836 and/or an area of tissue around electrode 836 from fluid in a lumen. In some embodiments, frame 853 may conduct heat away from electrode 836 and/or the tissue near electrode 836. For example, the heat may be conducted to a heat sink cooling electrode 836 and/or the tissue around electrode 836.

Figure 9A:
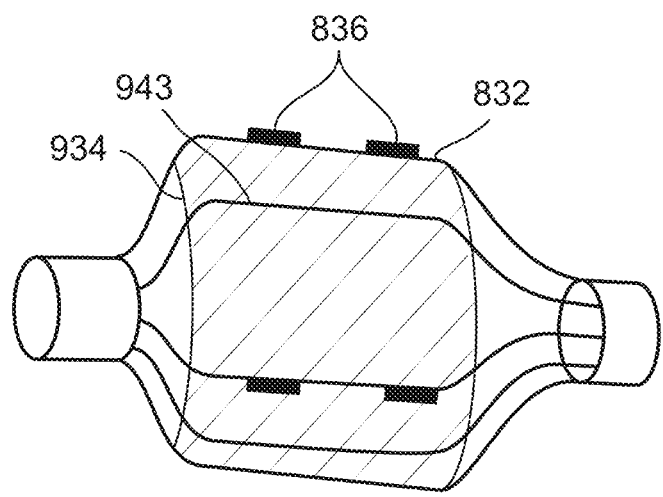
FIGS. 9A-B illustrate a support structure and insulator in accordance with some embodiments of the present invention.
Figure 9B:
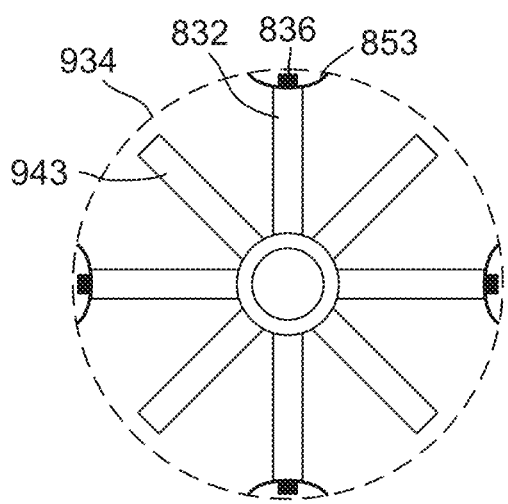

FIGS. 9A-B, illustrate an insulating membrane 934 wrapped around a support structure in accordance with some embodiments of the current invention. Electrodes 836 may optionally protrude through holes in membrane 934 to contact the tissue. Frame 853 may hold membrane against the tissue around electrode 836 optionally insulating electrode 836 from a bodily fluid. Optionally, additional support members (for example members 943) may supply further support to membrane 934. Alternatively or additionally, frame 853 may be an insulator. In some embodiments may not a surrounding membrane 934. Alternatively or additionally a nitinol stent type support structure may support electrodes 836 and/or a frame 853 and/or a membrane 934. Exemplary nitinol stent type support structures are illustrated for in FIGS. 6A-B and 10.

Figure 10:
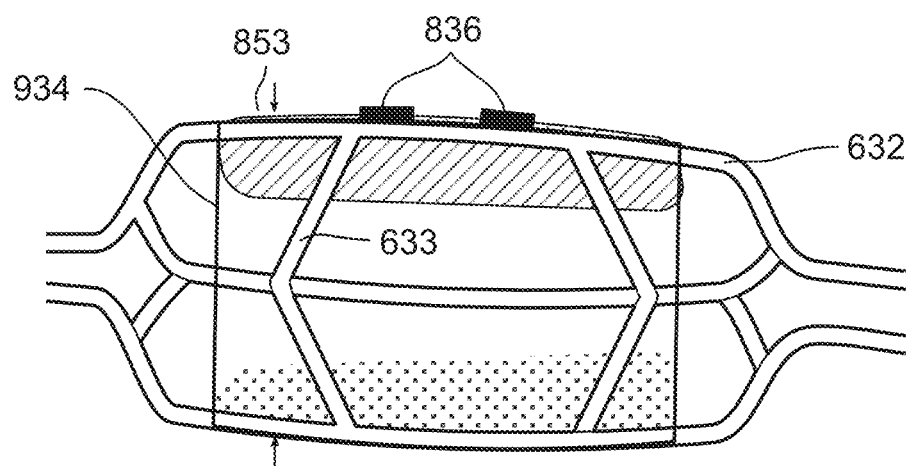
FIG. 10 illustrates a laser-cut tube support structure and insulator in accordance with some embodiments of the present invention.

FIG. 10 illustrates a nitinol support structure with a surrounding membrane 934 and a frame 853 around electrodes 836 in accordance with some embodiments of the current invention. Optionally, an ablation device (for example as illustrated in FIG. 8 and/or FIGS. 9A-B and/or FIG. 10) may include one or more markers for example similar to markers 455*a,b*.

Figure 11A:
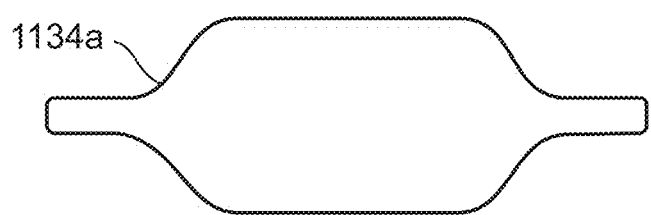
FIGS. 11A-B illustrate a laminar support structure in accordance with some embodiments of the present invention.
Figure 11B:
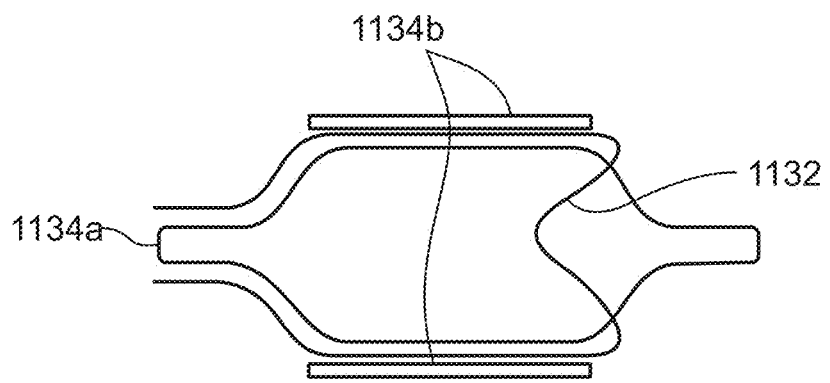

In some embodiments, a ablation device may include a laminated membrane. For example as shown in FIGS. 11A-B, the membrane may be formed by laminating several layers of polymers with similar and/or different characteristics. Optionally, the laminated membrane may tend to expand outwardly. For example, the laminated membrane may push outward against a lumen wall, insulating the wall from fluid inside the lumen.

FIG. 11A illustrates a balloon 1134*a* insulator in accordance with some embodiments of the current invention. In some embodiments, balloon 1134*a* may be fitted inside a support structure 1132. Optionally, support structure 1132 may include a stent type support (for example as illustrated in FIGS. 6A-B). As illustrated for example in FIG. 11B, balloon 1134*a* may be welded to the support structure 1132. For example, welding may be by adhering balloon 1134*a* to a layer of polymer film 1134*b* in a lamination that sandwiches the support structure 1132 between the two layers (balloon 1134*a* and film 1134*b*). Further layers may optionally be added, for example to achieve a desired stiffness, elasticity, deformability, heat conductivity and/or electrical conductivity. Optionally, the ends of the balloon may be trimmed and/or removed to produce a passageway for fluid flow. Optionally, heat conducting elements may be introduced between the layers to preferentially cool particular areas of an ablation zone (for example a portion of the target tissue and/or an electrode).

Figure 12A:
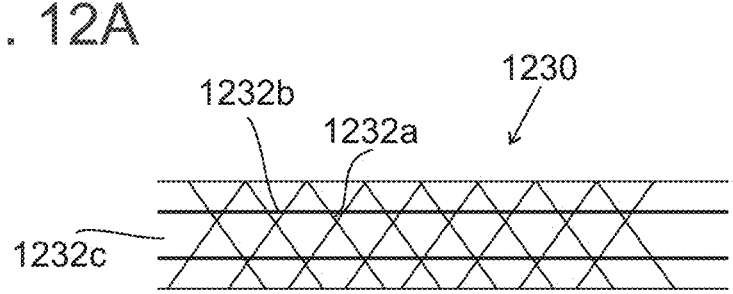
FIGS. 12A-B illustrate a support structure including braided wires in accordance with some embodiments of the present invention.
Figure 12B:
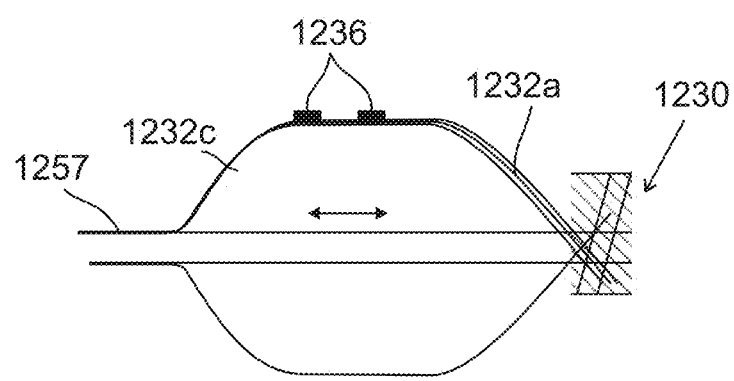

In some embodiments, a braid of wires that forms a catheter shaft may be expanded to form a basket support for an insulator. For example, spiral element 732 of FIG. 7 may form part of a braided casing of a catheter. FIGS. 12A-B illustrate a catheter having braided elements in accordance with some embodiments of the current invention. For example, the braided elements may include one or more insolated Copper wires 1232a (for example copper with a polyimide insulation [Cu-Pi]) and/or one or more stainless steel [SST] wires 1232b. Optionally, Cu-Pi wires 1232a may be used to carry current and/or signals between a control unit, an RF signal generator and/or an electrode in the catheter. The catheter may also include one or more axial wires 1232c. The axial wires 1232c may for example be formed of Nitinol. For example, at a distal end of a catheter one or more nitinol wire 1232c may form a support structure; for example as illustrated in FIG. 12B. One or more Cu-Pi wire 1232a may carry a current and/or a signal between a signal generator and/or a receiver at a proximal end of the catheter and an electrode 1236 and/or a sensor and/or an electrode at a distal end of the catheter, for example as illustrated in FIG. 12B. Alternatively or additionally an expanding basket may be made of radial and/or spiral elements. Alternatively or additionally, a pull wire 1257 may be provided to deploy an expanding support structure. For example, in some embodiments, a guidewire tube may be used as a pull wire.

In some embodiments, the wires that form the basket may not be formed as a separate distal head to the catheter. Optionally, the wires that form the basket may be part of the conductors that come all the way through a catheter's shaft 1230. For example, a conductor (for example bringing current and/or a signal to or from an electrode) may be an insulation-coated nitinol wire. The wire may provide structural support, for example forming a spline strut. The same wire may also serve as an electrical conductor.

FIGS. 13A-C and FIGS. 14A-C illustrate embodiments of insulators and support structures formed as a malecot in accordance with some embodiments of the current invention. For example in FIGS. 13A-C tubing inside of a catheter expands out of slits in a malecot break configuration. Alternatively or additionally in FIGS. 14A-C a malecot extends out a distal end of a catheter.

Figure 13A:
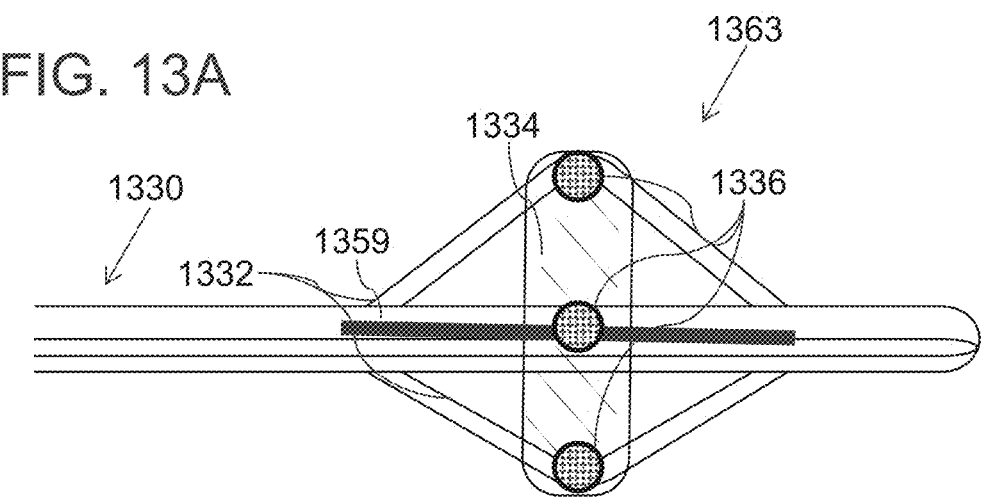
FIGS. 13A-C illustrate a support structure including a break-out malecot in accordance with some embodiments of the present invention.
Figure 13B:
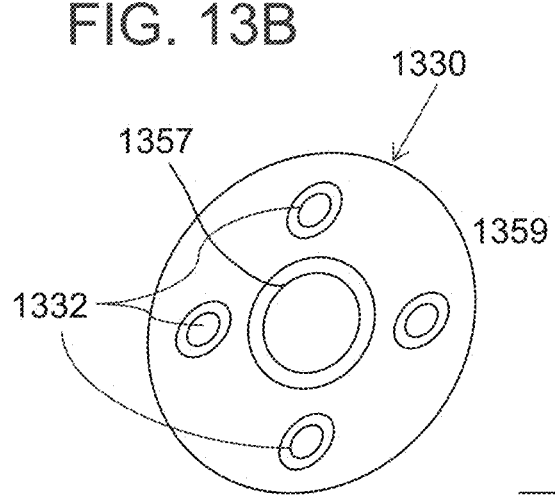
Figure 13C:
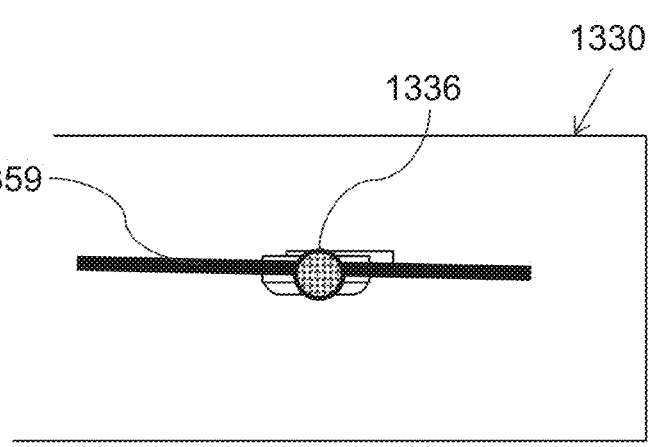

In some embodiments, for example as illustrated in FIGS. 13A-C a catheter may have malecot 1363 and/or a multi-lumen profile with wire breakout slits 1359. FIG. 13A illustrates malecot 1363 in an expanded configuration in accordance with some embodiments of the present invention. At slits 1359 an outer sheath 1330 of the catheter may allow an inner tubing 1332 to expand into a basket shape during actuation. Conducting wires may optionally run through a lumen of tubing 1332. Electrodes 1336 and/or markers may be mounted on tubing 1332 and/or connected to an RF signal generator and/or signal receiver via the conducting wires. An insulator may include a membrane 1334 surrounding sheath 1330 at the location of slits 1359. When malecot 1363 expands it may be surrounded by membrane 1334. Membrane 1334 may have openings through which electrodes 1336 protrude to contact the tissue to be ablated. FIGS. 13B,C illustrate malecot 1363 in a retracted configuration. An inner lumen of the catheter may include a pull wire 1357 that may be used to expand and/or retract malecot 1363. Alternately or additionally the insulator may include a frame mounted on tubing 1332 surrounding electrodes 1336 for example similar to frame 853 of FIG. 8. Alternately or additionally an insulating membrane may surround tubing 1332 on the inside of sheath 1330. When the malecot 1363 is expanded, the alternative membrane may expand out of slits 1359 in a star shape.

Figure 14A:
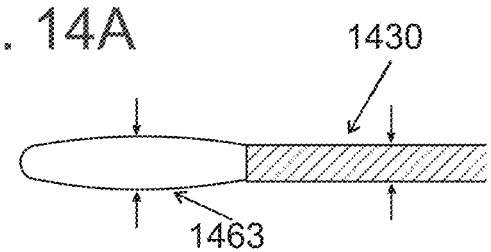
FIGS. 14A-C illustrate a support a distal-extending malecot in accordance with some embodiments of the present invention.
Figure 14B:
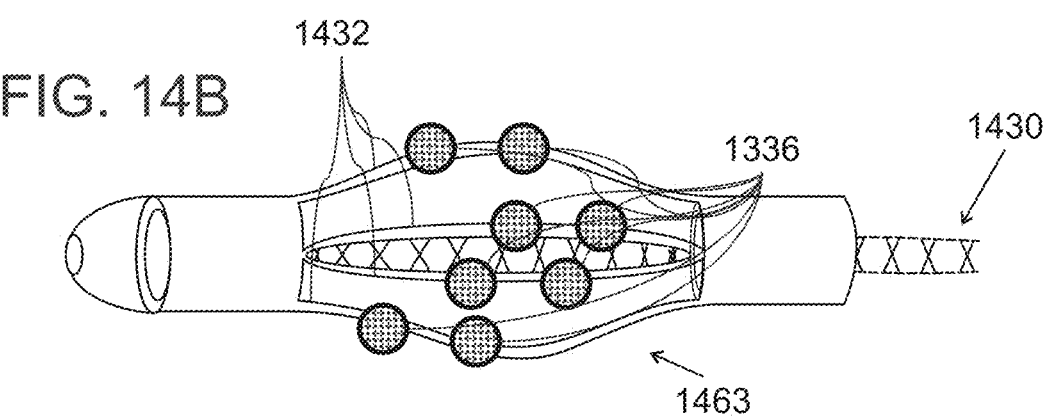
Figure 14C:
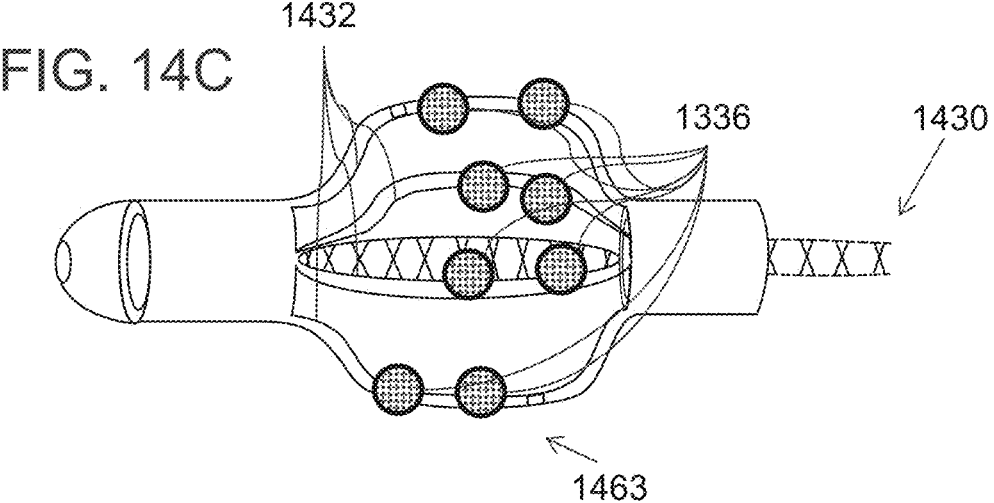

FIGS. 14A-C illustrate a malecot 1463 extending out of a distal end of a catheter in accordance with some embodiments of the current invention. Optionally malecot 1463 may be formed of a laser cut Nitinol tube. Optionally malecot 1463 may have an retracted configuration where it fits in a catheter 1430 with an outer diameter of less than 2 mm and/or an extended configuration wherein malecot 1463 extends out of the distal end of catheter 1430. In some embodiments in the extended configuration malecot may have a diameter of less than 3 mm. For example malecot 1463 is illustrated in an extended configuration in FIGS. 14A and 14B. In the extended configuration struts 1432 of malecot 1463 may be slightly expanded. Optionally malecot 1463 may have an expanded configuration. For example, FIG. 14C illustrates malecot 1463 in an expanded configuration. For example, an axial compressing force (for example exerted by pulling a pull wire) may cause malecot 1463 to expand radially from the extended configuration to the expanded configuration. The degree of expansion and/or pressure on the tissue to be ablated may optionally be user controllable according to the tension on the pull cord. In the expanded configuration the diameter of malecot 1463 may be larger than the diameter in the extended configuration and less than for example 7.5 mm Malecot 1463 may carry electrodes 4136 and/or markers. Malecot 1463 may include an insulating sleeve for example similar to membrane 1334 and/or an insulating frame (for example similar to frame 854) for insulating electrodes 1336.

Figure 15A:
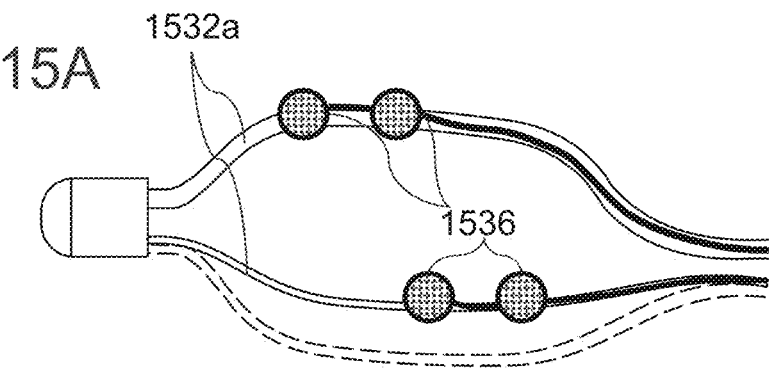
FIGS. 15A-B illustrate a hydraulic support structure in accordance with some embodiments of the present invention.
Figure 15B:
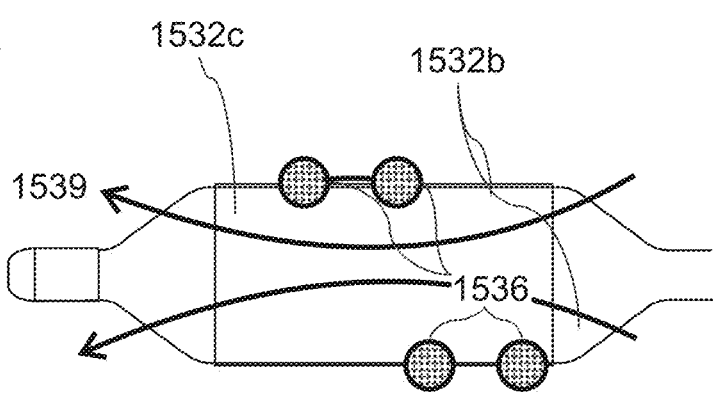

FIGS. 15A-B illustrate insulators for an ablation device that may be expanded by hydraulic pressure in accordance with some embodiments of the current invention. For example, FIG. 15A illustrates an exemplary support structure including a hydraulic struts 1532a. FIG. 15B illustrates an exemplary insulator for an ablation device including a double hydraulic sleeve 1532c which may be inflated by increasing hydraulic pressure between the sleeves. Lumen fluids (for example blood) may flow 1539 through a passageway in the inner sleeve. Struts 1532a and or sleeve 1532c may optionally carry electrodes 1536 and/or an insulator (for example a membrane sleeve and/or a frame around electrodes 1536 and/or wires 1532b and/or markers.

Insulating sleeves and/or hydraulic sleeves may be constructed for example by blow molding. Blow molding may optionally allow for secure mounting of a membrane proximal and distal to an expandable support.

Figure 16A:
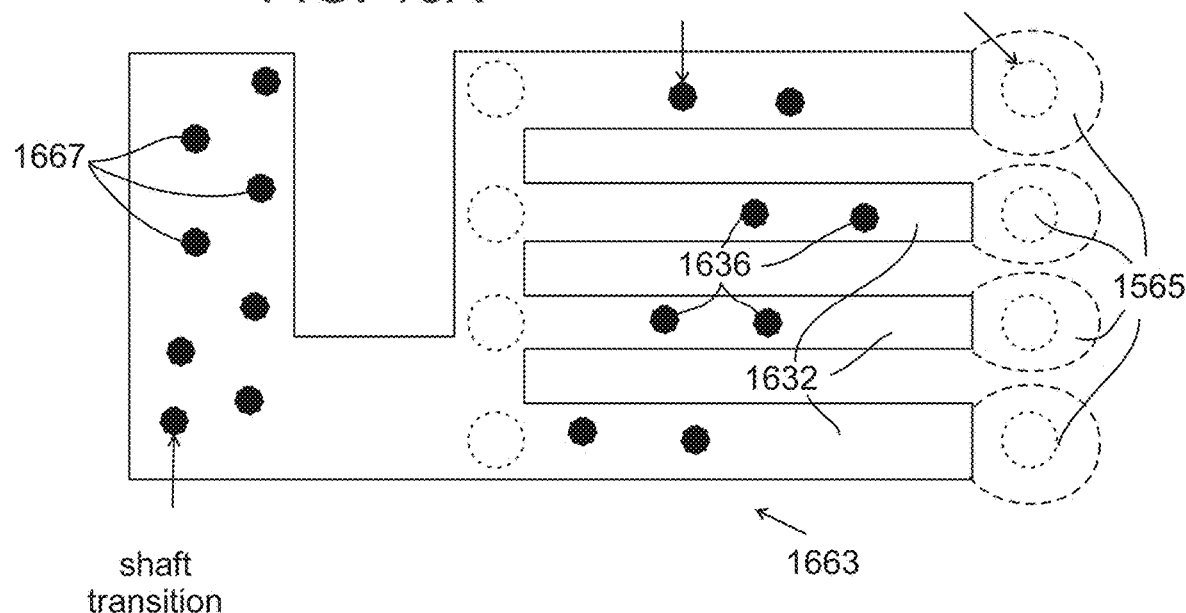
FIGS. 16A-C illustrate a printed circuit board support structure and insulator in accordance with some embodiments of the present invention.
Figure 16B:
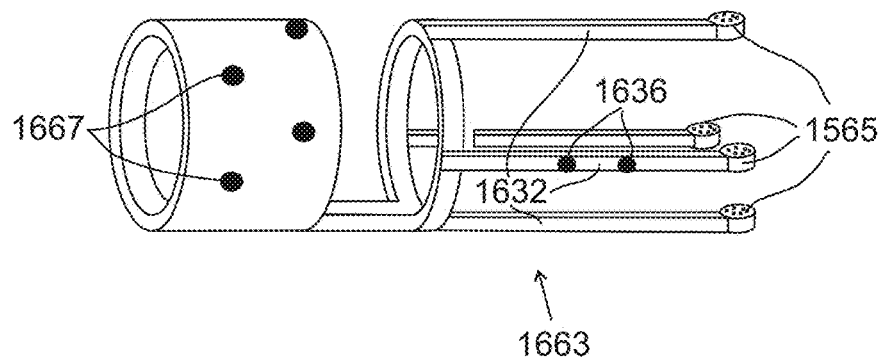
Figure 16C:
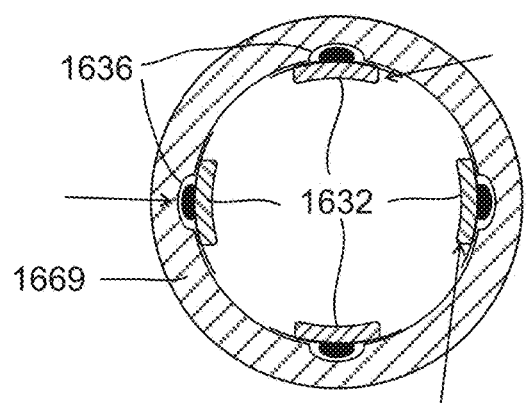

FIG. 16A-C illustrate a flexible circuit board ablation device in accordance with some embodiments the present invention. For example a flexible printed circuit board (PCB) may be made of polyimide (PI). Circuits may optionally be printed on one or more surfaces. FIG. 16A illustrates a flexible circuit board 1663 for an ablation device laid out flat, according to some embodiments of the current invention. Board 1663 may include electrodes 1636 that may optionally be mounted on flexible struts 1632. The ablation device may optionally be connected to a support structure, for example a nitinol basket and/or an inflatable strut. The ablation device may include connections to other devices for example electrical leads and/or rings 1565 for connecting to structural supports and/or shaft transition pads 1667 through which electrical connection is made between the printed circuit board and the wires within the catheter's shaft that transmit and/or receive energy to/from an RF generator and/or receiver. FIG. 16B illustrates circuit board 1663 rolled up in a retracted state for mounting to a catheter. FIG. 16C illustrates a cross sectional view of an embodiment of board 1663 inserted in a body lumen 1669 in an expanded state. Electrodes 1636 may optionally contact with the walls of lumen 1669. Struts 1632 may optionally serve as an insulator. For example, struts 1632 may contact the wall of lumen 1669 in an area surrounding electrodes 1636. For example, struts 1632 may prevent shunting of current from electrodes 1636 to fluid inside of lumen 1669. Alternatively and/or additionally, struts 1632 may transfer heat from electrodes 1636 and or the wall of lumen 1669 to the lumen fluid. For example the thickness and/or material of struts 1632 may be adjusted to achieve a desired conductivity and/or resistance to electrical current and/or heat flow. For example, a heat sink may be printed on board 1663 and/or a channel may be printed to conduct heat from one or more electrodes 1636 and/or tissue in contact with board 1663 to a heat sink and/or lumen fluid. For example heat may be conducted and/or absorbed by a high heat conductivity channel and/or a high heat capacity element such as a metal insert and or channel in the insulator. Optionally the geometry of a heat sink and/or heat conduction channel may be adjusted to cool a particular area more than another area. For example, a highly heat conductive region may be formed near an electrode, preferentially cooling an area near the electrode. Further from the electrode the heat conductivity may be smaller. Thus, cooling may be increased near the electrode where overheating is more prevalent.

5 Control Unit

Figure 17:
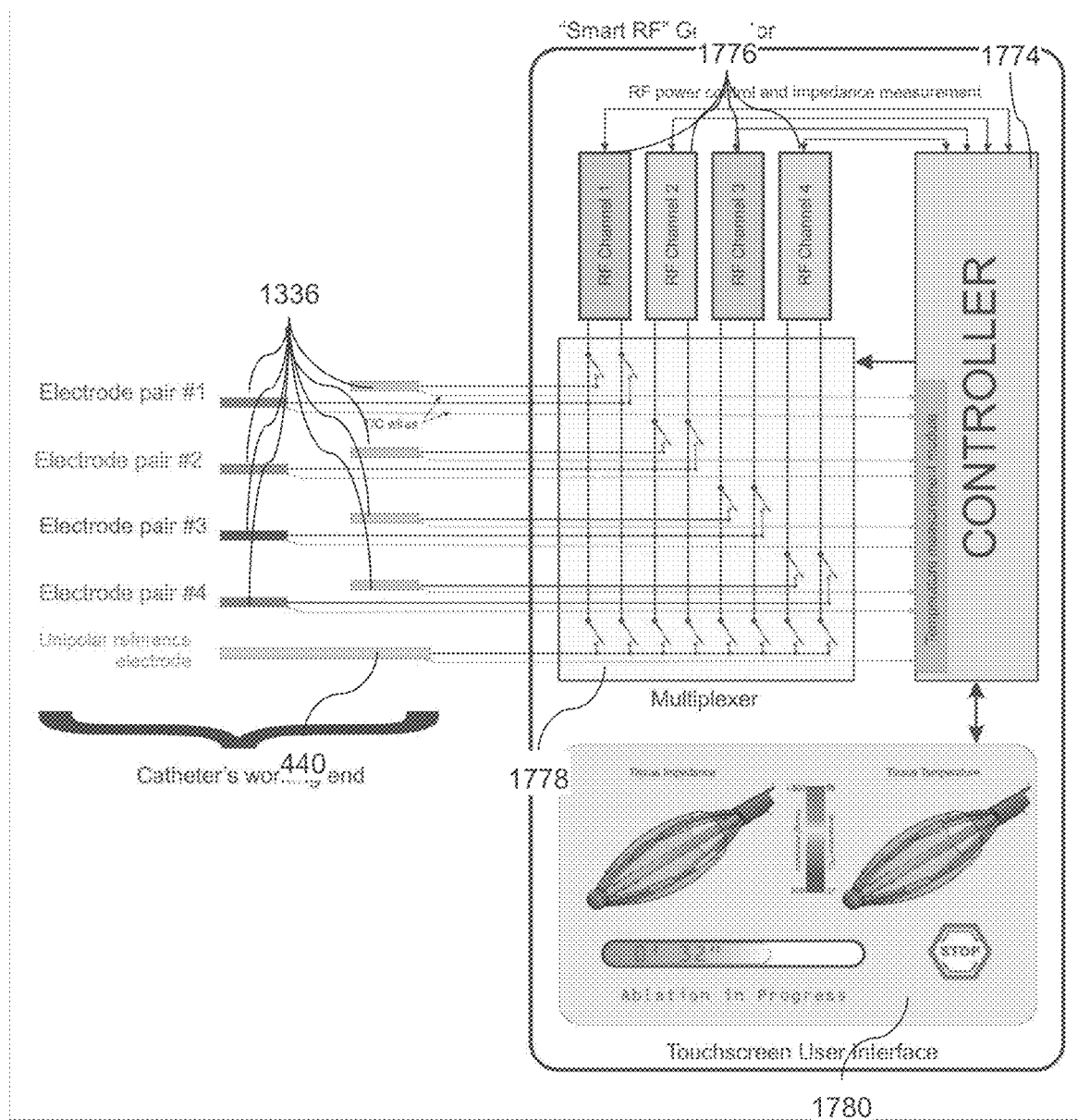
FIG. 17 illustrates control unit in accordance with some embodiments of the present invention.

FIG. 17 illustrated a control unit for an ablation device in accordance with some embodiments of the current invention. For example a control unit may include one or more radio frequency (RF) channels 1776. The control unit may optionally have a number of channels 1776 that convey electrical signals for bipolar ablation between multiple electrode pairs (for example between specific pairs and/or any combination of a large number of electrodes, e.g., electrodes 436*a-h*, electrodes 1336 etc., mounted for example on a spine of the catheter's working end). Alternatively or additionally, RF channels 1776 may convey a signal for unipolarly ablation (for example between one or more ablation electrodes e.g., electrodes 1336 and a dispersive electrode, e.g., electrode 440). In some embodiments the dispersive electrode may be located inside a catheter (for example a shaft electrode). For example, an internal dispersive electrode may be placed in contact with fluid (e.g. blood) inside a lumen (e.g. a blood vessel) wherein the ablation is taking place.

In some embodiments, signal of a single frequency may be conveyed for one or more electrodes, e.g., to pair of electrodes in bipolar ablation or one or more electrodes in unipolar ablation). In some embodiments, signals of a plurality of frequencies may be conveyed for one or more electrodes. For example, in bipolar ablation: a first pair of electrodes may receive signal of a first frequency and a second pair of electrodes may receive signal of a second frequency. For example, in unipolar ablation: a first electrode may receive signal of a first frequency and a second electrode may receive signal of a second frequency.

In some embodiments, a phase difference of the signal conveyed to a pair of electrodes may be controlled, e.g., by controller 1774. Optionally, the phase difference may be controlled based on impedance and/or temperature measurements. In some embodiments, other parameters of a signal conveyed to one or more electrodes may be controlled, e.g., based on impedance and/or temperature measurements.

Selecting electrodes may optionally be according to a switch configuration. The selection may optionally be set by a multiplexer 1778. Optionally, RF channels 1776 may have the means to measure electrode/tissue impedance under whatever selection is set by the switch configuration of the multiplexer 1778. The RF channels 1776, the switches and/or multiplexor 1778 may be controlled by a central controller 1774 (for example the central controller 1774 may include a processor, for example a microcontroller and/or single-board computer). The control unit may include receiver that is able to measure temperature inside the lumen (for example by means of a thermocouple attached at the location of one, some or all of the electrodes and/or at other locations). The control unit may include a user interface 1780, for example a graphical user interface (GUI), e.g. presented on a touch screen.

In some embodiments, electrode impedance measurements may be used to estimate contact between electrode and tissue. Alternatively or additionally impedance measurements may be used as surrogate for thermal contact between electrode interface and target tissue. Optionally, RF power, electrode temperature, and electrode impedance may be used to estimate power being converted to heat at electrode/tissue interface. The estimated contact and/or estimated power may optionally be used to calculate energy transferred to target tissue and/or resulting target tissue temperature. Temperature and/or impedance measurements may be used in real-time to determine whether to apply unipolar or bipolar ablation. Optionally, other sensors inputs may be used in real-time to determine whether to apply unipolar or bipolar ablation. In some embodiments, the operator (e.g., a physician) may determine whether to apply unipolar or bipolar ablation, optionally based on temperature and/or impedance measurements which may be displayed to the operator. Additionally or alternatively, temperature and/or impedance measurements may be used in real-time to control power and duration of ablation. The power and/or duration of ablation may optionally be used to ensure quality of lesion formation. The generator may estimate lesion quality for an individual electrode and/or for an area between electrodes. The algorithms may optionally alert a user that lesion formation has been completed when the quality of lesion at each electrode location reaches a predetermined range. The algorithm may instruct changing which electrodes are powered and/or the power level and/or frequency. The instructions may be dependent on a spatial differential in progress of ablation. The changing may be automatic and/or, the algorithm may recommend changes to a user and wait for user input before making changes. For example, if ablation is progressing faster at a first electrode of a pair of electrodes than at a second electrode, the algorithm may instruct switching to unipolar ablation at the second electrode. For example, if ablation is localized too much at the electrode locations, the algorithm may instruct changing to a frequency that penetrates tissue better.

In some embodiments, the control unit may measure complex bipolar and/or unipolar electrode impedance. For example impedance may be measured at the ablation frequency and/or at another frequency. Optionally, measurements may be made while ablating based on the ablation signal. Alternatively or additionally, impedance measurements may be made when not ablating. For example, during a interruption in ablation, impedance may be measured using an auxiliary signal. The auxiliary signal may be generated by an RF generator of one or more of channels 1776. The auxiliary signal may optionally meet the requirements of an auxiliary current not meant to cause any physiological effect. In some embodiments, electrode Impedance measurements shall be possible within the 100Ω to 1 kΩ range with a minimum accuracy of 5%, and within the 1001Ω to 2 kΩ range with a minimum accuracy of 10%. Minimum repeatability within the 100Ω to 2 kΩ range may optionally be 5%. In some embodiments, ablation interruptions of less than 100 ms may be made for measuring impedance during ablation segments. Optionally, an auxiliary signal for impedance measurements may have the same frequency as ablation signals and/or an auxiliary signal for impedance measurements may have a different frequency from an ablation signal. Optionally, impedance measurements may be conveyed between a pair of electrodes being used for an ablation and/or an impedance measurement may be conveyed between electrodes between which there is no current ablation treatment. For example, during an interruption in bipolar ablation impedance may be measured between a disperse electrode and one ablation electrode of the active bipolar pair. Optionally, impedance measurements may be taken at a rate greater than 100 samples/s.

6 Evoked Response

In some embodiments, evoked response may be used for determining a treatment location and/or measuring ablation progress. For example, target sites may optionally be located by finding regions where electrical stimulation delivered through the electrodes causes a significant vasocontractile response. Once ablation is started, changes in vasocontractile response to stimulation may be used to control the delivery of energy until a certain dampening of the vasocontractile response indicates desired extent of the effect of the ablation. Alternatively or additionally, the evoked electrical response to stimulus may be measured to find ablation sites and/or to estimate the extent of the effect of the ablation.

Figure 20:
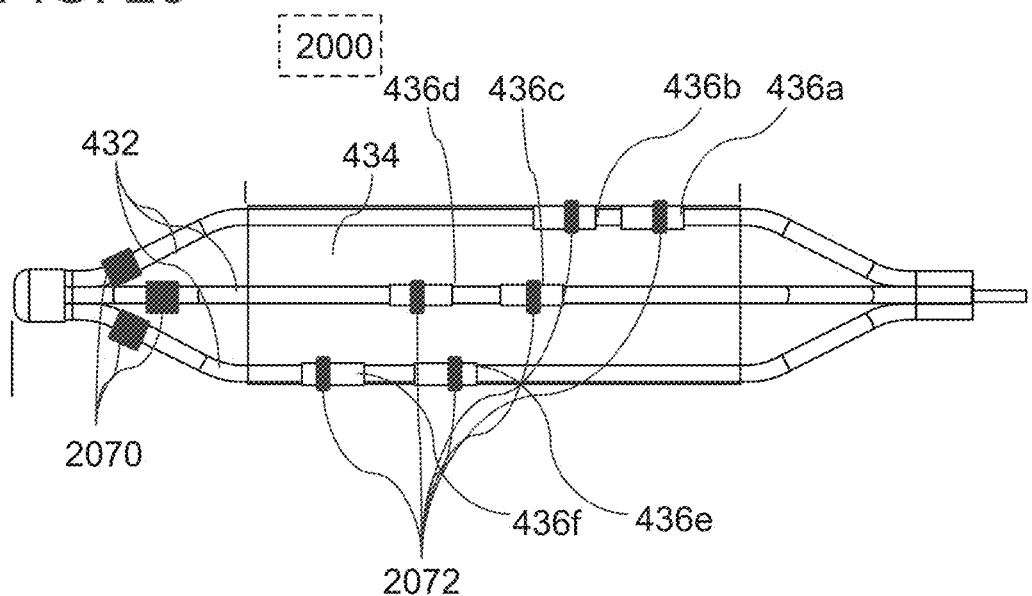
FIG. 20 illustrates an ablation device included sensors for evoked response in accordance with some embodiments of the present invention.
Figure 21A:
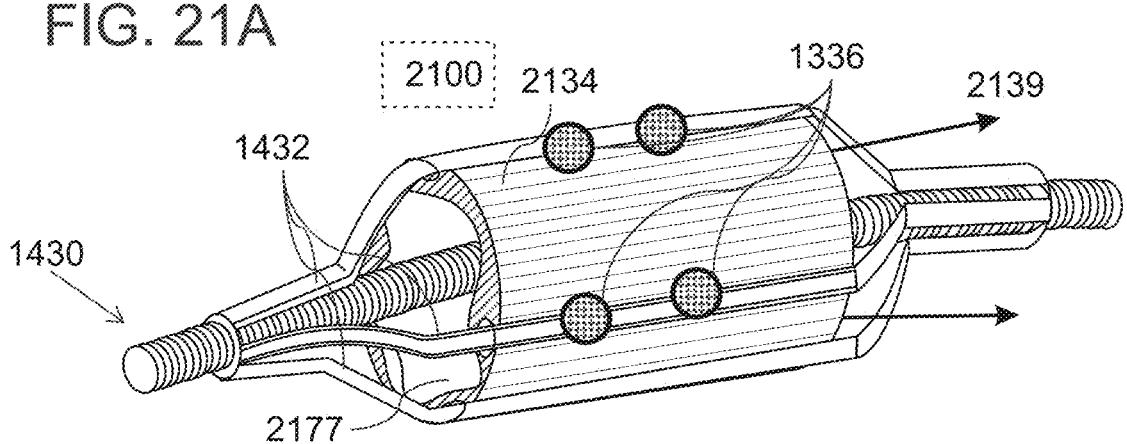
FIGS. 21A-B illustrate an alternate ablation device included sensors for evoked response in accordance with some embodiments of the present invention.
Figure 21B:
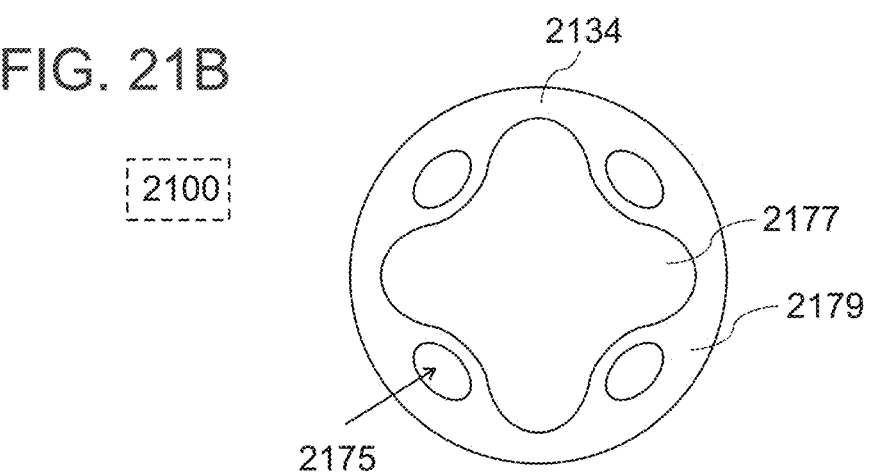

For example a catheter may be supplied with an apparatus for measuring vasoconstriction (for example through balloon pressure, strain on supports, pressure on a transducer [for example measuring blood pressure in the lumen being ablated and/or elsewhere], electrical signals [picked up for example by an antenna and/or an electrode in the catheter or elsewhere] and/or impedance measurements, for example as illustrated in FIG. 20 and FIGS. 21A-B).

Figure 18:
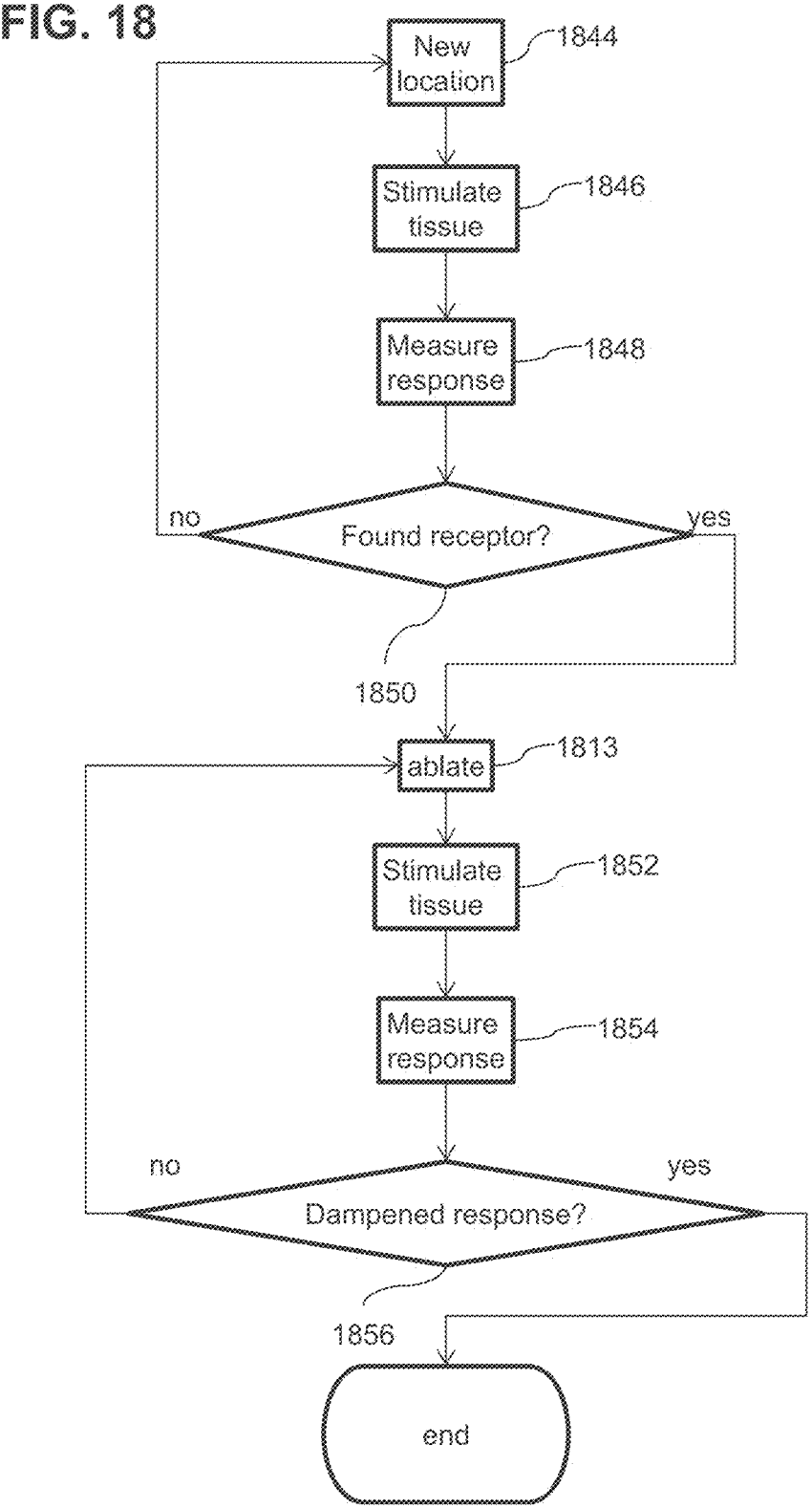
FIG. 18 is a flow chart illustration of a method of ablation and/or measuring evoked response in accordance with some embodiments of the present invention.

FIG. 18 illustrates an exemplary method of finding a receptor (for example a receptor may include perivascular renal nerve) and/or ascertaining ablation progress via evoked response, in accordance with some embodiments of the invention. In some embodiments, a stimulation electrode (which could include for example an ablation electrode) is positioned 1844 at a location wherein there may be an ablation candidate receptor. The catheter may then be set up, for example expanding a basket and/or an insulator against the walls of the lumen. The tissue may optionally be stimulated 1846 for example via an electrical signal. The response may be measured 1848 (for example the vasoconstriction and/or the electrical response). For example, a fast and/or strong response may indicate the presence of a receptor. If a receptor is not found 1850, then the simulation electrode is positioned 1844 at a new location. If a receptor is found 1850, then the ablation 1813 may proceed. Ablation 1813 may include bipolar ablation (for example bipolar ablation 112 as described hereinabove) and/or unipolar ablation (for example unipolar ablation 114 as described hereinabove). In some embodiments a catheter may have multiple electrodes and/or electrode pairs. If some electrodes are located near a receptor and others not, ablation may optionally occur in those electrodes near receptors before moving the catheter. In place of and/or in addition to the tests described herein above evoked response may be used to measure ablation progress. During ablation, current application may be interrupted and an electrical signal may be transmitted to stimulate 1852 the tissue. The evoked response to stimulation may then be measured 1854 (for example the vasoconstriction and/or the electrical response). If the response is not yet damped 1856 enough, then ablation 1813 may continue. If the response is damped 1856 enough, then the process ends (for example either the ablation session ends and/or the process restarts finding another site and optionally ablating that site).

In some embodiments, the method illustrated in FIG. 18 may be used for determining a treatment location in a body of a patient e.g., by stimulating a tissue and detecting an elicited response. For example, treatment locations may be located by finding regions where electrical stimulation delivered through the electrodes causes a significant vasocontractile response. Once ablation is started, changes in vasocontractile response to stimulation may be used to control the delivery of energy for example a certain dampening of the vasocontractile response indicates desired extent of lesion formation. Optionally, the evoked response may be measured in the intravascular space (for example by a blood pressure sensor in the catheter) and/or elsewhere in the body (for example through a blood pressure or blood flow sensor elsewhere in the body and/or from a location external to the body, for example through a blood pressure sensor, heart rate sensor, or plethysmography sensor).

In some embodiments, an evoked response may include an electrical reaction signal produced in response to a stimulus. Optionally, the stimulus may be applied inside a lumen of the patient, for example by a device on the ablation catheter. Optionally, a target site may be identified as a region where delivering a stimulation causes a significant evoked response. For example, a target for ablation may include a nerve terminal. Optionally, the stimulus may include an electrical signal. The evoked response may be measured for example as an electrogram. Optionally, the evoked response may be measured in the intravascular space (for example by electrodes of the catheter) and/or elsewhere in the body (for example at a nerve location elsewhere in the body and/or from a location external to the body (for example using an external electrode or extrabody imaging). Once ablation is started, changes in evoked response to stimulation may optionally be used to control the delivery of energy until a certain dampening of the evoked response is detected. The dampened response may optionally indicate a desired extent of lesion formation. When sufficient dampening is detected, ablation may optionally be stopped.

Figure 19:
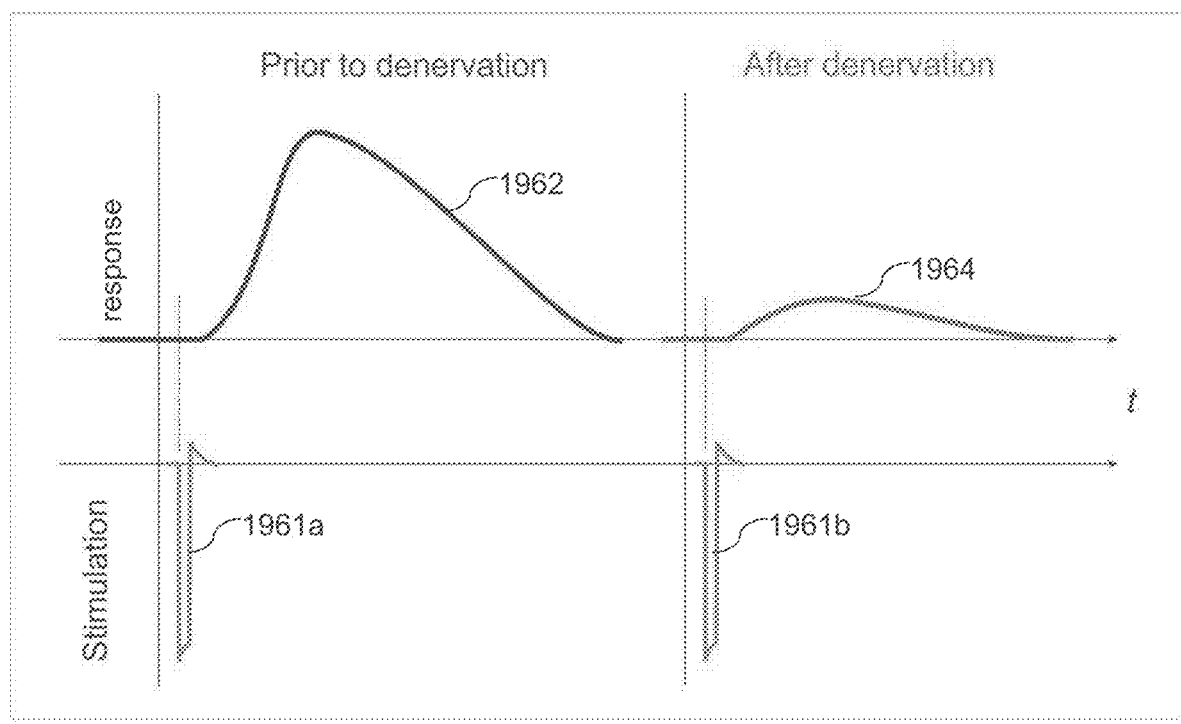
FIG. 19 illustrates simulated measurements of an evoked response in accordance with some embodiments of the present invention.

FIG. 19 illustrates an exemplary stimulation and evoked response, in accordance with some embodiments of the invention. For example, curve 1961a illustrates a stimulation to the receptors before ablation (either while searching for receptors or at the beginning of ablation). The abscissa shows time (for example a few milliseconds) and the ordinate may include for example the voltage of the signal and/or the current. The measured return signal is represented by graph 1962. The measured signal may include a change in pressure in a balloon due to vasoconstriction and/or a stress and/or a strain on a support of a basket (for example support 432) and/or a change electrical potential and/or impedance measured on the tissue. For example, curve 1961b illustrates a stimulation to the receptors after ablation. For example, curve 1964 illustrates the dampening of the return signal after successful ablation.

FIG. 20 illustrates an ablation device 2000 capable of measuring evoked response in accordance with some embodiments of the current invention. Ablation device 2000 may, for example, include a support structure similar to that of FIG. 4C (for example including struts 432). Ablation device 2000 may option include markers (for example similar to markers 455a,b—not illustrated), electrodes 436a-h, an insulator (for example a membrane 434) and/or other components or structures described above. For example, the support structure, markers, electrodes 436a-h and/or insulator may be similar to one, some and/or any of the embodiments above. Optionally, ablation device 2000 may include one or more sensors to sense evoked response. For example, a strain gauge 2070 may measure evoked vasoconstriction response and/or resultant squeezing of the support structure. Alternately or additionally, ablation device 2000 may include a pressure transducer to measure the fluid pressure inside a lumen. Ablation device 2000 may include exemplary thermocouples 2072 for measuring temperature near the ablation electrodes 436a-h.

FIGS. 21A-B illustrate a perspective and a cross sectional view respectively of an alternate ablation device 2100 capable of measuring evoked response in accordance with some embodiments of the invention. Ablation device 2100 may, for example, include a malecot support structure similar to that of FIGS. 14A-C (for example including struts 1432). Ablation device may option include markers (for example similar to markers 455a,b—not illustrated), electrodes 1336 and/or an insulator 2134. Ablation device 2100 may include other components or structures described above. For example, the support structure, markers, sensors, electrodes sensors and/or insulator may be similar to one, some and/or any of the embodiments above. Optionally, ablation device 2100 may be configured to sense evoked response. For example, insulator may be configured to sense pressure and/or shape changes caused by evoked vasoconstriction response and/or resultant squeezing of the support structure. For example, insulator 2134 may include an internal liquid filled cavity 2179. Changes in the shape of insulator 2134 may induce changes in the internal pressure in cavity 2179 and may be sensed by a pressure transducer. Alternatively or additionally, ablation device 2100 may be constructed of multiple layers of material which may produce an electrical response (for example a change in resistance) under strain. The electrical response may be sensed and/or used detect an evoked response. The materials of insulator 2134 and or the fluid between layers may be chosen to provide a heat sink and/or heat conductor, for example for conducting heat away from the ablation zone. Insulator 2134 may include a central passageway 2177 through which lumen fluids may flow 2139. Optionally, struts 1432 may pass through support lumens 2175 in insulator 2134.

Figure 22A:
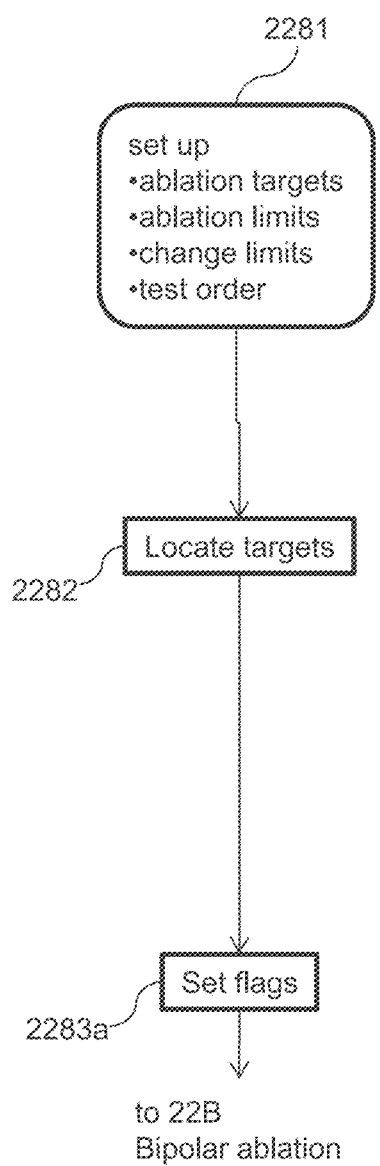
FIGS. 22A-C are a flow chart illustration of a control algorithm for combined unipolar and bipolar ablation.
Figure 22B:
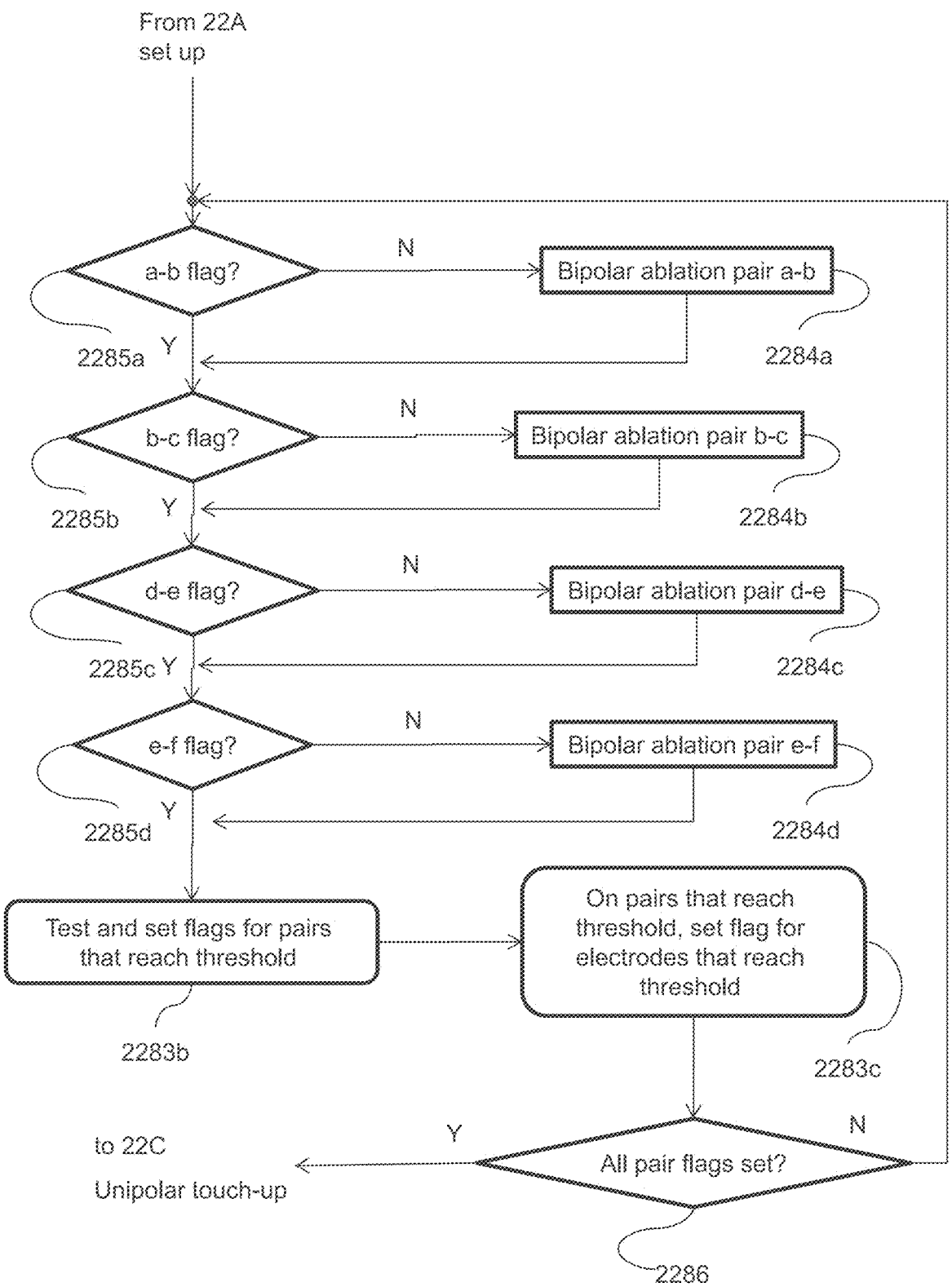
Figure 22C:
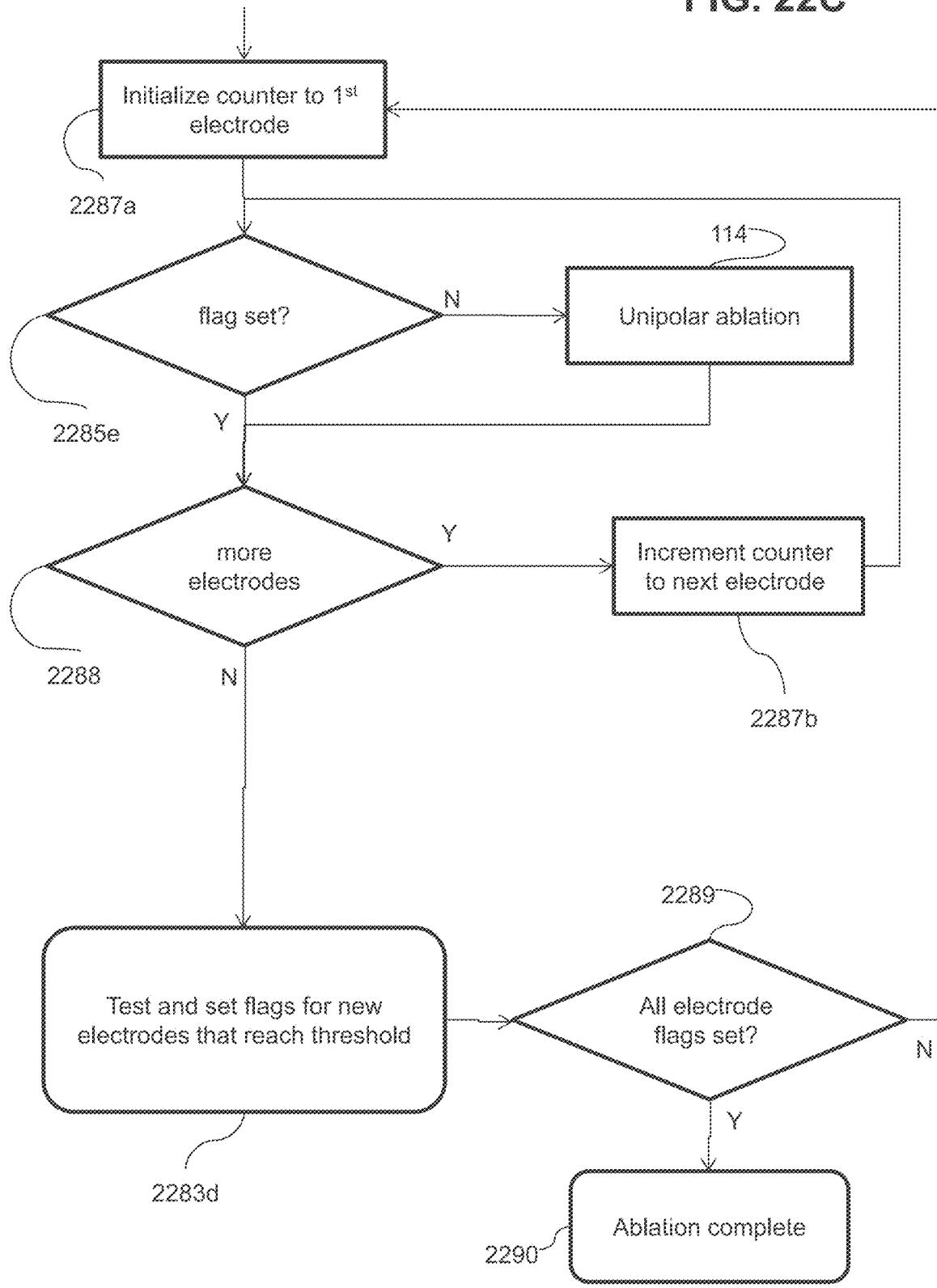

FIGS. 22A-C are flowcharts illustrating a control algorithm for ablation according to some embodiments of the current invention.

Optionally the process may start with setting up 2281 ablation parameters according to some embodiments of the current invention. For example, in some embodiments an initial impedance range may be set. Initial impedance may optionally be measured by conveying an auxiliary signal between two or more electrodes. There may optionally be one range for bipolar impedance (for example for conveying a signal between two ablation electrodes) and/or another range for unipolar impedance (for example for conveying a signal between an ablation electrode and a dispersive electrode). A high initial impedance may in some embodiments be a sign of poor contact between an electrode and the target tissue. A low initial impedance may be a sign that a signal is being shunted away from the target (for example because an insulator is not properly contacting tissue surrounding an ablation electrode). If the initial impedance is outside of the set range, for a particular electrode and/or pair of electrodes, the electrode and/or electrodes may optionally not be used for ablation until they are repositioned.

In some embodiments, a ablation duration may be set. Optionally the ablation duration may be the length of ablation time at a single location will continue if measured ablation parameters do not reach a target and/or a limit. For example the ablation duration may be set between 45 seconds and 3 minutes (e.g., between 45 seconds and 1 minutes, between 1 minute and 3 minutes, between 2 minutes and 3 minutes etc.) with a default value of 45 seconds.

In some embodiments, a target ablation temperature may be set. Optionally, the operator may set the target ablation temperature. Additionally or alternatively, the target ablation temperature may be set automatically (e.g., by controller 174), optionally based on impedance measurements or other measurements. For example the target temperature may be set between 65° C. and 75° C. (e.g., 65° C., 70° C., 75° C. etc.) with a default value of 65° C. For example if a measured tissue temperature reaches the target value, ablation may be stopped.

In some embodiments a bipolar impedance change limit and/or target may be set. For example if a change (for example a reduction and/or increase) in impedance measured between two ablation electrodes over the course of an ablation reaches or surpasses the limit and/or target, ablation may be stopped Impedance may be measured during ablation (for example the impedance that is overcome conveying the ablation signal between the two electrodes). Alternatively or additionally impedance may be measured during an interruption in ablation (for example the impedance overcome conveying an auxiliary signal between the two electrodes may be measured). An auxiliary signal may have the same frequency as an ablation signal and/or it may have a different frequency. Alternatively or additionally an unipolar impedance change limit and/or target may be set. For example a unipolar change in impedance may be measured between an ablation electrode and a dispersive electrode. For example, during an interruption in bipolar ablation, a unipolar impedance may be measured between one or each of the bipolar electrodes and a dispersive electrode. In some embodiments one or more ranges of impedance may be set. For example, if during ablation a unipolar and/or bipolar impedance falls outside of its respective range, ablation may be stopped.

In the set up 2281 phase an order of measurement may be set according to some embodiments of the current invention. For example in some cases an interruption time period and/or interruption interval may be set. For example, during ablation, after passing of a time period equal to an interruption interval, ablation may be interrupted for an interruption time period. For example the interruption time interval may range between 5 and 30 seconds and the interruption time period may range between 10 ms and 100 msec. The measurements to be made during ablation and/or during an interruption may be set.

Ablation may optionally start by locating 2282 targets, for example, according to the method illustrated in FIG. 18 and the accompanying description. Alternatively or additionally, ablation may proceed at all electrodes that pass an initial impedance test without searching for receptors. Each ablation electrode that fails the initial impedance test and/or the target test may optionally be flagged 2283*a*. The flag may indicate that this electrode at this location should not be used for ablation. For example a pair of electrodes may be flagged 2283*a* due to high initial impedance (indicating for example poor contact with the target tissue) and/or due to lack of initial evoked response (indicating for example that there are no target structures in the vicinity of the electrode).

FIG. 22B illustrates a flow chart of an algorithm for controlling bipolar ablation to achieve a specified distribution of ablation and/or lesions in a tissue according to some embodiments of the current invention. In some embodiments, the flowchart illustrated in FIG. 22B may be following the flowchart illustrated in FIG. 22A. In some embodiments, bipolar ablation 2284*a*, 2284*b*, 2284*c*, 2284*d* may be applied, at selected pairs of electrodes. For each pair of electrodes bipolar ablation may produce a lesion distributed in a target zone between and/or around the electrodes. For example bipolar ablation may check 2285*a*, 2285*b*, 2285*c*, 2285*d* and performed bipolar ablation at all pairs that are not flagged. Bipolar ablation may proceed, for example, as illustrated in FIG. 2. Bipolar ablation may proceed simultaneously for some or all of the selected pairs of electrodes and/or serially for each selected pair. When a pair of electrodes reaches an ablation limit and/or target level, the pair may be flagged 2283*b*. Ablation limit and/or target level may be identical for all pair of electrodes. Alternatively, ablation limit and/or target level may be different between two or more pairs of electrodes, e.g., based on the pairs of electrodes location in reference to the ablated tissue. Flagging 2283*b* an electrode pair may indicate that no more ablation should be applied to the flagged pair of electrodes (for example because the ablation already progressed to a target level and/or to a limit).

In some embodiments a sub-zone of a respective target zone may be selected for further ablation. For example, bipolar ablation 2284*a* between electrodes a and electrode b may produce a lesion distributed in a vicinity of electrode a, in a vicinity of electrode b and/or between electrodes a and b. The progress of ablation may be tested in a subzone, for example in the vicinity of an individual electrode. For example a flag may indicate that ablation reached a target and/or a limit in a subzone. For example, if tissue in vicinity of an individual electrode reaches a target temperature (and/or remains within a target temperature range for a predetermined time period) that electrode may be flagged 2283*c*. The quality of lesion factor calculated from the unipolar impedance, electrode temperature, applied power and duration of ablation may be used as a sign of the ablation level in the vicinity of the ablation electrode. When the quality of lesion reaches a target value the associated electrode may be flagged 2283*c*. In some embodiments, all eligible pairs unipolar ablation may be checked 2286 if they are all flagged, bipolar ablation may be deemed to be finished.

In some embodiments unipolar ablation may finish off ablation in a non-flagged subzone. Optionally, estimates of quality of ablation may be used to estimate the spatial distribution of a lesion and/or ablation progress. The of quality of ablation may be estimated in various subzones based on measured indicators in those subzones. For example lesion formation may be estimated near an ablation electrode (for example by measuring unipolar impedance at the ablation electrode), between ablation electrodes (for example by measuring bipolar impedance between the electrodes) and/or at the location of another sensor (for example near a temperature sensor based on measured temperature). Based on the estimated spatial distribution of lesion formation, ablation may be undertaken in selected areas. For example ablation may be used to achieve a predetermined and/or desired spatial distribution of a lesion (for example by ablating in a subzone where the lesion had not achieved the desired level) and/or ablation progress.

FIG. 22C illustrates a flow chart of an algorithm control of unipolar ablation to achieve a specified distribution of ablation and/or lesions in a tissue according to some embodiments of the current invention. In some embodiments, the flowchart illustrated in FIG. 22C may be following the flowchart illustrated in FIG. 22B. In some embodiments, after determining that ablation and/or lesion formation has reached a target level somewhere in the zone of each active bipolar pair of ablation electrodes, the control algorithm will loop through the individual of electrodes of the pairs of bipolar electrodes. The algorithm may optionally select zones (for example in the vicinity of individual electrodes) for unipolar ablation. For example unipolar ablation may be used to finish off ablation at a location where a state of ablation has not reached a target level. For example the state of ablation in the vicinity of an ablation electrode may be evaluated by calculating a quality of lesion factor from the unipolar impedance (between an ablation electrode and the dispersive electrode), ablation electrode temperature, applied power and duration of ablation In some embodiments, a counter is initialized to point 2287*a* to a first electrode and its flag may be checked. In the case of an electrode that has not been flagged (2885*e*:N), the electrode is selected for unipolar ablation 114 for example as illustrated in FIG. 3. After performing unipolar ablation, if there are more electrodes that have not been treated 2288 then the next counter may be incremented to point 2287*b* to the next electrode. If the electrode has been flagged (2285*e*:Y) (indicating that ablation has progressed to a limit and/or target level near the electrode) then it may be skipped. If there are more electrodes that have not been treated (2288:Y) then the counter may be incremented to point 2287*b* to the next electrode. In some embodiments unipolar ablation may be used to ablate regions deeper in the tissue that those regions reached by bipolar ablation.

In some embodiments after unipolar ablation 114 the state of ablation may be evaluated for in the vicinity of the selected electrode. Optionally, evaluation of the state of ablation may be based on sensor results. For example when an impedance between the ablation electrode and a dispersive electrode has reached a target value the state of ablation may be evaluated as complete and/or the ablation electrode may be flagged 2283*d*. Alternatively or additionally when a temperature in the vicinity of the electrode has reached a target value and/or remained at a target value for a predetermined time period, ablation in the vicinity of the electrode may be evaluated as complete and/or the ablation electrode may be flagged 2283*d*. Preferably, when a quality of lesion factor calculated from the unipolar impedance (between an ablation electrode and the dispersive electrode), ablation electrode temperature, applied power and duration of ablation has reached a target value the state of ablation may be evaluated as complete and/or the ablation electrode may be flagged 2283*d*. In some embodiments state of ablation may be evaluated during ablation (for example based on temperature measurements and/or the impedance of the ablation signal). Alternatively or additionally the state of ablation may be evaluated during interruptions of ablation and/or after ablation (for example based on the impedance of an auxiliary signal). Electrodes which have reached an ablation target and/or a limit may be flagged 2283*d*. Optionally, if there remain electrodes which have not been flagged 2289:N than the counter may be reinitialized to point 2287a to the first electrode and the process repeated. The process may optionally continue until all the electrodes are flagged 2289:Y as having reached an ablation target and/or limit. When all the electrodes the electrodes are flagged 2289:Y, the ablation may be deemed complete 2290. For example after completing 2290 ablation, the catheter may be moved to a new spot the process restarted for example by setting up the catheter 2281. Alternatively or additionally, the treatment may be stopped and the catheter removed.

In some embodiments, pairs of ablation electrodes for bipolar ablation may be mounted on a single support member and/or on separate support members. In some embodiments, electrode pairing may be fixed. Alternatively or additionally, in some embodiments electrode pairs may be variable. For example, according to the example of FIG. 20, in some embodiments, electrode 436a may always be paired with electrode 436b in bipolar ablation. Alternatively or additionally in some embodiments electrode 436a may always be paired with electrode 436d in bipolar ablation. Alternatively or additionally in some embodiments pairing may vary, for example 436a may be paired with electrode 436b in one bipolar ablation and the switched for example to be paired with electrode 436d in another ablation.

According to some embodiments of the current invention, all and/or any portion of the steps of FIGS. 22A-C may be carried out in a single ablation session and/or while the ablation catheter and/or the electrodes remain in the same position. For example a single session may last for a time period ranging between 15 minutes to two hours (e.g. 15 minutes to 30 minutes, 30 minutes to an hour, an hour to two hours). For example a single ablative electrode may perform at a single location during a single session any, some and/or all of the functions of bipolar ablation and/or unipolar ablation and/or sensing an indicator of ablation progress and/or sensing an indicator of lesion formation. The sensing may be for example by sensing an impedance. Optionally the impedance may be to a unipolar signal and/or bipolar signal. The signal may include for example an ablation signal and/or an auxiliary signal. Optionally the functions may be preformed serially and/or repeatedly in any order. In some embodiments, some of the functions may be performed simultaneously. A controller may optionally instruct any or all of the above functions in a single session while the catheter and/or the electrode is in a single location. The controller may optionally evaluate a level of ablation and/or ablate a single location, zone and/or subzone and/or multiple locations, zones and/or subzones in a single session and/or with a catheter and/or the electrodes at a single location. A catheter may optionally include a control unit enabling performance of the above functions as described above, for example with a single ablations electrode in a single location in a single ablation session.

It is expected that during the life of a patent maturing from this application many relevant technologies will be developed and the scope of the terms used herein is intended to include all such new technologies a priori. As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An ablation device comprising:
    an ablation catheter comprising:
        a plurality of ablation electrodes;
        a dispersive electrode; and
        one or more sensors detecting an indicator of ablation progress;
    and a controller programmed to:
        receive from said one or more sensors an indicator of progress of a bipolar ablation process between a pair of said plurality of ablation electrodes, wherein, during bipolar ablation by said pair of electrodes of said plurality of ablation electrodes, ablation with a unipolar signal is not performed using any electrode of the pair of said plurality of ablation electrodes,
        select one electrode from said pair of ablation electrodes based on said indicator of progress of the bipolar ablation process;
        instruct to ablate with a unipolar signal between said dispersive electrode and said one electrode selected based on the indicator of progress of the bipolar ablation process,
        wherein the controller is programmed to operate the bipolar ablation before ablation with the unipolar signal.

2. The ablation device of claim 1, wherein said controller is further programmed to analyze a level of ablation from said received indicator and wherein said controller is programmed to instruct to ablate a zone wherein said analyzed level of ablation is below a target level.

3. The ablation device of claim 1, wherein said controller is further programmed to instruct said bipolar ablation process.

4. The ablation device of claim 1, wherein said controller is further programmed to instruct stopping said bipolar ablation process based on said received indicator.

5. The ablation device of claim 1, wherein output of said one or more sensors indicates a preliminary distribution of lesion formation in a target tissue and wherein said controller is programmed to instruct said unipolar signal to achieve a predetermined distribution of lesion formation in said target tissue.

6. The ablation device of claim 1, wherein said one or more sensors detect an impedance between two electrodes selected from said plurality of ablation electrodes and said dispersive electrodes.

7. The ablation device of claim 1, wherein said controller is further programmed to:
    instruct conveying of an auxiliary signal between a pair of electrodes selected from said ablation electrodes and said dispersive electrode during an interruption in said bipolar ablation process and wherein said one or more sensors are sensitive to an impedance between two of said plurality of ablation electrodes or between a dispersion electrode and an ablation electrode.

8. The ablation device of claim 1, wherein said plurality of electrodes includes at least four pairs of electrodes distributed helically along a lumen.

9. The ablation device of claim 1, wherein said controller is further programmed to evaluate a contact of an electrode with a target tissue based on an impedance between said electrode and a dispersive electrode.

10. The ablation device of claim 1, wherein said one or more sensors detect temperature of at least one of the target tissue and temperature of at least one of said plurality of ablation electrodes.

11. The ablation device of claim 1, further comprising:
    an insulator electrically insulating at least one of said plurality of ablation electrodes from a fluid in a lumen.

12. The ablation device of claim 1, wherein said dispersive electrode is in contact with a fluid inside of a lumen.

13. The ablation device of claim 1, wherein said one or more sensors include a plurality of sensors and wherein said controller is further programmed to estimate a spatial distribution of a lesion in the tissue based on output from the plurality of sensors.

14. The ablation device of claim 13, wherein said controller is further programmed to instruct said ablation with a unipolar signal to modify the spatial distribution of lesion formation to achieve a predetermined spatial distribution of lesion formation.

15. The ablation device of claim 1, wherein said controller is programmed to instruct the one electrode to repeatedly function, in a single location during a single ablation session, as a bipolar ablation electrode and unipolar ablation electrode.

16. The ablation device of claim 1, wherein a radio frequency channel of the controller conveys electrical signals for both the bipolar ablation process and for ablation with the unipolar signal.

17. The ablation device of claim 16, wherein the radio frequency channel conveys an electrical signal between the one electrode and another one of said pair of said plurality of ablation electrodes for the bipolar ablation process, and wherein the radio frequency channel conveys an electrical signal between the one electrode and said dispersive electrode for performing unipolar ablation.

* * * * *